US010543025B2

(12) United States Patent
Rabiner et al.

(10) Patent No.: US 10,543,025 B2
(45) Date of Patent: *Jan. 28, 2020

(54) SYSTEMS AND METHODS FOR INTERNAL BONE FIXATION

(71) Applicant: IlluminOss Medical, Inc., East Providence, RI (US)

(72) Inventors: Robert A. Rabiner, Barrington, RI (US); Mark A. Drew, Boston, MA (US)

(73) Assignee: IlluminOss Medical, Inc., East Providence, RI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/652,147

(22) Filed: Jul. 17, 2017

(65) Prior Publication Data

US 2017/0311996 A1    Nov. 2, 2017

Related U.S. Application Data

(63) Continuation of application No. 14/535,913, filed on Nov. 7, 2014, now Pat. No. 9,717,542, which is a
(Continued)

(51) Int. Cl.
*A61B 17/00*   (2006.01)
*A61B 17/68*   (2006.01)
(Continued)

(52) U.S. Cl.
CPC .......... *A61B 17/7097* (2013.01); *A61B 17/68* (2013.01); *A61B 17/7275* (2013.01);
(Continued)

(58) Field of Classification Search
CPC . A61B 17/7097; A61B 17/68; A61B 17/7275; A61B 17/7291; A61B 17/8836; A61B 2017/00557
(Continued)

(56) References Cited

U.S. PATENT DOCUMENTS 3,485,520 A    12/1969  Alexander
4,271,839 A     6/1981  Fogarty et al.
(Continued)

FOREIGN PATENT DOCUMENTS

DE    40 28 466    3/1992
EP    0 709 698    5/1996
(Continued)

OTHER PUBLICATIONS

USPTO Office Action in U.S. Appl. No. 15/834,459 dated Mar. 30, 2018.
(Continued)

*Primary Examiner* — Pedro Philogene
(74) *Attorney, Agent, or Firm* — Greenberg Traurig, LLP; David J. Dykeman; Roman Fayerberg

(57) ABSTRACT

Internal bone fixation devices and methods for using the devices for repairing a weakened or fractured bone are disclosed herein. A device for use in repairing a fractured bone includes a delivery catheter having an elongated shaft with a proximal end, a distal end, and a longitudinal axis therebetween, wherein the delivery catheter has an inner void for passage of at least one reinforcing material and an inner lumen for passage of a light source; a conformable member releasably engaging the distal end of the delivery catheter, wherein the conformable member moves from a deflated state to an inflated state when the at least one reinforcing material is delivered to the conformable member; and an adapter releasably engaging the proximal end of the delivery catheter for receiving the light source and the at least one reinforcing material.

20 Claims, 12 Drawing Sheets

Related U.S. Application Data continuation of application No. 13/730,521, filed on Dec. 28, 2012, now Pat. No. 8,906,031, which is a continuation of application No. 12/858,924, filed on Aug. 18, 2010, now Pat. No. 8,366,711, which is a continuation of application No. 11/903,123, filed on Sep. 20, 2007, now Pat. No. 7,811,284.

(60) Provisional application No. 60/880,646, filed on Jan. 16, 2007, provisional application No. 60/858,202, filed on Nov. 10, 2006.

(51) Int. Cl.
  A61B 17/70 (2006.01)
  A61B 17/72 (2006.01)
  A61B 17/88 (2006.01)

(52) U.S. Cl.
  CPC ...... *A61B 17/7291* (2013.01); *A61B 17/8836* (2013.01); *A61B 2017/00557* (2013.01)

(58) Field of Classification Search
  USPC .... 606/60, 62–68, 92–94, 190–197; 604/21; 600/101, 116, 178, 408
  See application file for complete search history.

(56) References Cited

U.S. PATENT DOCUMENTS

| | | | |
|---|---|---|---|
| 4,280,233 A | 7/1981 | Raab |
| 4,294,251 A | 10/1981 | Greenwald et al. |
| 4,313,434 A | 2/1982 | Segal |
| 4,341,691 A | 7/1982 | Anuta |
| 4,369,772 A | 1/1983 | Miller |
| 4,414,608 A | 11/1983 | Furihata |
| 4,422,719 A | 12/1983 | Orcutt |
| 4,433,898 A | 2/1984 | Nasiri |
| 4,462,394 A | 7/1984 | Jacobs |
| 4,466,435 A | 8/1984 | Murray |
| 4,562,598 A | 1/1986 | Kranz |
| 4,686,973 A | 8/1987 | Frisch |
| 4,697,584 A | 10/1987 | Haynes |
| 4,735,625 A | 4/1988 | Davidson |
| 4,870,953 A | 10/1989 | DonMichael et al. |
| 4,888,024 A | 12/1989 | Powlan |
| 4,892,550 A | 1/1990 | Huebsch |
| 4,904,391 A | 2/1990 | Freeman |
| 4,961,424 A | 10/1990 | Kubota et al. |
| 4,963,151 A | 10/1990 | Ducheyne et al. |
| 4,969,888 A | 11/1990 | Scholten et al. |
| 5,030,093 A | 7/1991 | Mitnick |
| 5,049,157 A | 9/1991 | Mittelmeier et al. |
| 5,085,660 A | 2/1992 | Lin |
| 5,092,899 A | 3/1992 | Forte |
| 5,102,413 A | 4/1992 | Poddar |
| 5,108,404 A | 4/1992 | Scholten et al. |
| 5,112,333 A | 5/1992 | Fixel |
| 5,207,669 A | 5/1993 | Baker et al. |
| 5,222,958 A | 6/1993 | Chin |
| 5,295,733 A | 3/1994 | LeBegue |
| 5,295,962 A | 3/1994 | Crocker et al. |
| 5,303,718 A | 4/1994 | Krajicek |
| 5,316,550 A | 5/1994 | Forte |
| 5,336,699 A | 8/1994 | Cooke et al. |
| 5,372,598 A | 12/1994 | Luhr et al. |
| 5,376,123 A | 12/1994 | Klaue et al. |
| 5,391,144 A | 2/1995 | Sakurai et al. |
| 5,415,654 A | 5/1995 | Daikuzono |
| 5,423,850 A | 6/1995 | Berger |
| 5,432,876 A | 7/1995 | Appeldorn et al. |
| 5,443,468 A | 8/1995 | Johnson |
| 5,445,608 A | 8/1995 | Chen et al. |
| 5,462,552 A | 10/1995 | Kiester |
| 5,480,400 A | 1/1996 | Berger |
| 5,538,514 A | 7/1996 | Hawkins |
| 5,548,676 A | 8/1996 | Savage, Jr. |
| 5,554,111 A | 9/1996 | Morrey et al. |
| 5,556,429 A | 9/1996 | Felt |
| 5,571,204 A | 11/1996 | Nies |
| 5,658,310 A | 8/1997 | Berger |
| 5,658,963 A | 8/1997 | Qian et al. |
| 5,702,446 A | 12/1997 | Schenck et al. |
| 5,705,181 A | 1/1998 | Cooper et al. |
| 5,707,374 A | 1/1998 | Schmidt |
| 5,713,901 A | 2/1998 | Tock |
| 5,795,353 A | 8/1998 | Felt |
| 5,824,087 A | 10/1998 | Aspden et al. |
| 5,827,289 A | 10/1998 | Reiley et al. |
| 5,888,220 A | 3/1999 | Felt et al. |
| 5,897,557 A | 4/1999 | Chin et al. |
| 5,908,433 A | 6/1999 | Eager et al. |
| 5,930,424 A | 7/1999 | Heimberger et al. |
| 5,972,015 A | 10/1999 | Scribner et al. |
| 5,980,075 A | 11/1999 | Sheaffer |
| 5,980,253 A | 11/1999 | Oxman et al. |
| 5,987,199 A | 11/1999 | Zarian et al. |
| 5,989,230 A | 11/1999 | Frassica |
| 5,997,570 A | 12/1999 | Ligtenberg et al. |
| 6,008,264 A | 12/1999 | Ostler |
| 6,019,761 A | 2/2000 | Gustilo |
| 6,019,774 A | 2/2000 | Weiss et al. |
| 6,033,411 A | 3/2000 | Preissman |
| 6,039,762 A | 3/2000 | McKay |
| 6,042,380 A | 3/2000 | De Rowe |
| 6,048,346 A | 4/2000 | Reiley et al. |
| 6,053,917 A | 4/2000 | Sherman et al. |
| 6,059,789 A | 5/2000 | Dinger et al. |
| 6,066,154 A | 5/2000 | Reiley et al. |
| 6,077,265 A | 6/2000 | Werding et al. |
| 6,079,868 A | 6/2000 | Rydell |
| 6,103,203 A | 8/2000 | Fischer |
| 6,110,176 A | 8/2000 | Shapira |
| 6,121,341 A | 9/2000 | Sawhney et al. |
| 6,127,597 A | 10/2000 | Beyar et al. |
| 6,136,011 A | 10/2000 | Stambaugh |
| 6,140,452 A | 10/2000 | Felt et al. |
| 6,159,236 A | 12/2000 | Biel |
| 6,179,852 B1 | 1/2001 | Strickland et al. |
| 6,195,477 B1 | 2/2001 | Denuto et al. |
| 6,200,134 B1 | 3/2001 | Kovac et al. |
| 6,217,581 B1 | 4/2001 | Tolson |
| 6,223,085 B1 | 4/2001 | Dann et al. |
| 6,224,630 B1 | 5/2001 | Bao et al. |
| 6,235,043 B1 | 5/2001 | Reiley et al. |
| 6,241,734 B1 | 6/2001 | Scribner et al. |
| 6,248,110 B1 | 6/2001 | Reiley et al. |
| 6,248,131 B1 | 6/2001 | Felt et al. |
| 6,254,571 B1 | 7/2001 | Hart |
| 6,258,089 B1 | 7/2001 | Campbell et al. |
| 6,261,289 B1 | 7/2001 | Levy |
| 6,280,456 B1 | 8/2001 | Scribner et al. |
| 6,282,013 B1 | 8/2001 | Ostler et al. |
| 6,290,382 B1 | 9/2001 | Bourn et al. |
| 6,299,597 B1 | 10/2001 | Buscemi et al. |
| 6,306,177 B1 | 10/2001 | Felt et al. |
| 6,319,255 B1 | 11/2001 | Grundei et al. |
| 6,332,894 B1 | 12/2001 | Stalcup et al. |
| 6,336,914 B1 | 1/2002 | Gillespie, III |
| 6,336,930 B1 | 1/2002 | Stalcup et al. |
| 6,358,252 B1 | 3/2002 | Shapira |
| 6,387,098 B1 | 5/2002 | Cole et al. |
| 6,395,007 B1 | 5/2002 | Bhatnagar et al. |
| 6,416,531 B2 | 7/2002 | Chen |
| 6,416,737 B1 | 7/2002 | Manolagas et al. |
| 6,419,483 B1 | 7/2002 | Adam et al. |
| 6,423,055 B1 | 7/2002 | Farr et al. |
| 6,423,083 B2 | 7/2002 | Reiley et al. |
| 6,425,923 B1 | 7/2002 | Stalcup et al. |
| 6,440,444 B2 | 8/2002 | Boyce et al. |
| 6,443,988 B2 | 9/2002 | Felt et al. |
| 6,447,514 B1 | 9/2002 | Stalcup et al. |
| 6,458,375 B1 | 10/2002 | Gertzman et al. |
| 6,478,751 B1 | 11/2002 | Krueger et al. |
| 6,482,234 B1 | 11/2002 | Weber et al. |

(56) References Cited

U.S. PATENT DOCUMENTS

| | | |
|---|---|---|
| 6,485,512 B1 | 11/2002 | Cheng |
| 6,494,883 B1 | 12/2002 | Ferree |
| 6,524,251 B2 | 2/2003 | Rabiner et al. |
| 6,524,313 B1 | 2/2003 | Fassier et al. |
| 6,551,321 B1 | 4/2003 | Burkinshaw et al. |
| 6,551,337 B1 | 4/2003 | Rabiner et al. |
| 6,565,528 B1 | 5/2003 | Mueller |
| 6,579,277 B1 | 6/2003 | Rabiner et al. |
| 6,579,279 B1 | 6/2003 | Rabiner et al. |
| 6,605,056 B2 | 8/2003 | Eidenschink et al. |
| 6,620,185 B1 | 9/2003 | Harvie et al. |
| 6,623,505 B2 | 9/2003 | Scribner et al. |
| 6,632,235 B2 | 10/2003 | Weikel et al. |
| 6,648,881 B2 | 11/2003 | KenKnight et al. |
| 6,652,547 B2 | 11/2003 | Rabiner et al. |
| 6,652,587 B2 | 11/2003 | Felt et al. |
| 6,660,013 B2 | 12/2003 | Rabiner et al. |
| 6,679,873 B2 | 1/2004 | Rabiner et al. |
| 6,695,781 B2 | 2/2004 | Rabiner et al. |
| 6,695,782 B2 | 2/2004 | Rabiner et al. |
| 6,696,073 B2 | 2/2004 | Boyce et al. |
| 6,716,216 B1 | 4/2004 | Boucher et al. |
| 6,719,773 B1 | 4/2004 | Boucher et al. |
| 6,726,691 B2 | 4/2004 | Osorio et al. |
| 6,730,048 B1 | 5/2004 | Hare et al. |
| 6,733,451 B2 | 5/2004 | Rabiner et al. |
| 6,733,513 B2 | 5/2004 | Boyle et al. |
| 6,740,093 B2 | 5/2004 | Hochschuler et al. |
| 6,755,862 B2 | 6/2004 | Keynan |
| 6,783,530 B1 | 8/2004 | Levy |
| 6,802,835 B2 | 10/2004 | Rabiner et al. |
| 6,818,018 B1 | 11/2004 | Sawhney |
| 6,852,095 B1 | 2/2005 | Ray |
| 6,866,678 B2 | 3/2005 | Shenderova et al. |
| 6,869,442 B2 | 3/2005 | Cheng |
| 6,875,212 B2 | 4/2005 | Shaolian et al. |
| 6,885,246 B2 | 4/2005 | Tsutsui et al. |
| 6,887,246 B2 | 5/2005 | Bhatnagar et al. |
| 6,887,275 B2 | 5/2005 | Carchidi et al. |
| 6,899,713 B2 | 5/2005 | Shaolian et al. |
| 6,899,719 B2 | 5/2005 | Reiley et al. |
| 6,932,843 B2 | 8/2005 | Smith et al. |
| 6,964,667 B2 | 11/2005 | Shaolian et al. |
| 6,975,898 B2 | 12/2005 | Seibel |
| 6,979,341 B2 | 12/2005 | Scribner et al. |
| 6,981,981 B2 | 1/2006 | Reiley et al. |
| 7,001,431 B2 | 2/2006 | Bao et al. |
| 7,008,433 B2 | 3/2006 | Voellmicke et al. |
| 7,048,731 B2 | 5/2006 | Altshuler et al. |
| 7,052,498 B2 | 5/2006 | Levy et al. |
| 7,077,865 B2 | 7/2006 | Bao et al. |
| 7,124,067 B2 | 10/2006 | Ascenzi |
| 7,141,061 B2 | 11/2006 | Williams et al. |
| 7,144,414 B2 | 12/2006 | Harvie et al. |
| 7,153,305 B2 | 12/2006 | Johnson et al. |
| 7,156,861 B2 | 1/2007 | Scribner et al. |
| 7,156,880 B2 | 1/2007 | Evans et al. |
| 7,169,140 B1 | 1/2007 | Kume |
| 7,215,863 B1 | 5/2007 | Arenella et al. |
| 7,241,303 B2 | 7/2007 | Reiss et al. |
| 7,252,677 B2 | 8/2007 | Burwell et al. |
| 7,258,692 B2 | 8/2007 | Thelen et al. |
| 7,261,720 B2 | 8/2007 | Stevens et al. |
| 7,320,709 B2 | 1/2008 | Felt et al. |
| 7,341,601 B2 | 3/2008 | Eisermann et al. |
| 7,360,542 B2 | 4/2008 | Nelson et al. |
| 7,407,616 B2 | 8/2008 | Melikechi et al. |
| 7,419,450 B2 | 9/2008 | Ito |
| 7,427,295 B2 | 9/2008 | Ellman et al. |
| 7,465,318 B2 | 12/2008 | Sennett et al. |
| 7,547,319 B2 | 6/2009 | Segal et al. |
| 7,621,950 B1 | 11/2009 | Globerman et al. |
| 7,628,800 B2 | 12/2009 | Sherman et al. |
| 7,632,277 B2 | 12/2009 | Woll et al. |
| 7,632,291 B2 | 12/2009 | Stephens et al. |
| 7,666,205 B2 | 2/2010 | Weikel et al. |
| 7,722,620 B2 | 5/2010 | Truckai et al. |
| 7,740,656 B2 | 6/2010 | Mensah et al. |
| 7,744,555 B2 | 6/2010 | DiMauro et al. |
| 7,766,965 B2 | 8/2010 | Bao et al. |
| 7,771,476 B2 | 8/2010 | Justis et al. |
| 7,776,075 B2 | 8/2010 | Bruneau et al. |
| 7,806,900 B2 * | 10/2010 | Rabiner .............. A61B 17/7275 606/92 |
| 7,811,284 B2 * | 10/2010 | Rabiner .................. A61B 17/68 606/62 |
| 7,811,286 B2 | 10/2010 | Medoff |
| 7,811,290 B2 | 10/2010 | Rabiner |
| 7,842,040 B2 | 11/2010 | Rabiner et al. |
| 7,850,711 B1 | 12/2010 | Stone et al. |
| 7,857,748 B2 | 12/2010 | Williams et al. |
| 7,879,041 B2 * | 2/2011 | Rabiner .............. A61B 17/7097 606/92 |
| 7,912,539 B2 | 3/2011 | Doty et al. |
| 7,947,015 B2 | 5/2011 | Herweck et al. |
| 8,012,157 B2 | 9/2011 | Chang et al. |
| 8,034,071 B2 | 10/2011 | Scribner et al. |
| 8,123,807 B2 | 2/2012 | Kim et al. |
| 8,187,278 B2 | 5/2012 | Biel |
| 8,210,729 B2 | 7/2012 | O'Leary et al. |
| 8,211,121 B1 | 7/2012 | Quinn et al. |
| 8,226,659 B2 | 7/2012 | Rabiner et al. |
| 8,246,628 B2 | 8/2012 | Rabiner |
| 8,262,694 B2 | 9/2012 | Widomski et al. |
| 8,328,402 B2 | 12/2012 | O'Leary et al. |
| 8,348,956 B2 | 1/2013 | Rabiner |
| 8,366,711 B2 * | 2/2013 | Rabiner .................. A61B 17/68 606/63 |
| 8,403,968 B2 | 3/2013 | Rabiner et al. |
| 8,413,664 B2 | 4/2013 | Appling |
| 8,512,338 B2 | 8/2013 | Rabiner et al. |
| 8,523,901 B2 | 9/2013 | Rabiner et al. |
| 8,545,499 B2 | 10/2013 | Lozier et al. |
| 8,574,233 B2 | 11/2013 | Rabiner et al. |
| 8,668,701 B2 | 3/2014 | Rabiner et al. |
| 8,672,982 B2 | 3/2014 | Rabiner et al. |
| 8,684,965 B2 | 4/2014 | Rabiner et al. |
| 8,708,955 B2 | 4/2014 | Tilson et al. |
| 8,734,458 B2 | 5/2014 | O'Halloran |
| 8,734,460 B2 | 5/2014 | Rabiner et al. |
| 8,764,761 B2 | 7/2014 | Truckai et al. |
| 8,777,950 B2 | 7/2014 | Colleran et al. |
| 8,870,965 B2 | 10/2014 | Rabiner et al. |
| 8,906,030 B2 | 12/2014 | Rabiner et al. |
| 8,906,031 B2 * | 12/2014 | Rabiner .................. A61B 17/68 606/93 |
| 8,915,966 B2 | 12/2014 | Rabiner et al. |
| 8,936,382 B2 | 1/2015 | O'Leary et al. |
| 8,936,644 B2 | 1/2015 | Rabiner et al. |
| 8,939,977 B2 | 1/2015 | DiPoto et al. |
| 9,005,254 B2 | 4/2015 | Rabiner et al. |
| 9,050,079 B2 | 6/2015 | Rabiner et al. |
| 9,101,419 B2 | 8/2015 | Colleran et al. |
| 9,125,706 B2 | 9/2015 | Rabiner et al. |
| 9,144,442 B2 | 9/2015 | Rabiner et al. |
| 9,179,959 B2 | 11/2015 | Rabiner et al. |
| 9,216,049 B2 | 12/2015 | Rabiner et al. |
| 9,254,156 B2 | 2/2016 | Rabiner |
| 9,254,195 B2 | 2/2016 | Rabiner et al. |
| 9,265,549 B2 | 2/2016 | Rabiner |
| 9,427,289 B2 | 8/2016 | Rabiner et al. |
| 9,433,450 B2 | 9/2016 | Rabiner et al. |
| 9,687,281 B2 | 6/2017 | DiPoto et al. |
| 9,717,542 B2 * | 8/2017 | Rabiner .................. A61B 17/68 |
| 9,724,147 B2 | 8/2017 | Rabiner |
| 9,775,661 B2 | 10/2017 | Rabiner et al. |
| 9,855,080 B2 | 1/2018 | Rabiner et al. |
| 9,855,145 B2 | 1/2018 | Rabiner et al. |
| 10,111,689 B2 | 10/2018 | Rabiner et al. |
| 10,292,823 B2 | 5/2019 | Rabiner et al. |
| 2001/0011174 A1 | 8/2001 | Reiley et al. |
| 2001/0044626 A1 | 11/2001 | Reiley et al. |
| 2001/0055462 A1 | 12/2001 | Seibel |
| 2002/0032444 A1 | 3/2002 | Mische |

(56) References Cited

U.S. PATENT DOCUMENTS

| | | |
|---|---|---|
| 2002/0082600 A1 | 6/2002 | Shaolian et al. |
| 2002/0091424 A1 | 7/2002 | Biel |
| 2002/0156482 A1 | 10/2002 | Scribner et al. |
| 2002/0161373 A1 | 10/2002 | Osorio et al. |
| 2002/0165544 A1 | 11/2002 | Perren et al. |
| 2002/0198526 A1 | 12/2002 | Shaolian et al. |
| 2003/0028210 A1 | 2/2003 | Boyle et al. |
| 2003/0083642 A1 | 5/2003 | Boyd et al. |
| 2003/0105469 A1 | 6/2003 | Karmon |
| 2003/0114914 A1 | 6/2003 | Cheng |
| 2003/0156431 A1 | 8/2003 | Gozum et al. |
| 2003/0199850 A1 | 10/2003 | Chavez et al. |
| 2003/0212426 A1 | 11/2003 | Olson et al. |
| 2003/0229372 A1 | 12/2003 | Reiley et al. |
| 2004/0006341 A1* | 1/2004 | Shaolian ............ A61B 17/1671 606/86 A |
| 2004/0024388 A1 | 2/2004 | Altshuler |
| 2004/0034434 A1 | 2/2004 | Evans et al. |
| 2004/0059333 A1 | 3/2004 | Carl et al. |
| 2004/0059417 A1 | 3/2004 | Smith et al. |
| 2004/0092948 A1 | 5/2004 | Stevens et al. |
| 2004/0098015 A1 | 5/2004 | Weikel et al. |
| 2004/0117025 A1 | 6/2004 | Reindel |
| 2004/0133280 A1 | 7/2004 | Trieu |
| 2004/0167561 A1 | 8/2004 | Boucher et al. |
| 2004/0167625 A1 | 8/2004 | Beyar et al. |
| 2004/0225296 A1 | 11/2004 | Reiss et al. |
| 2004/0228142 A1 | 11/2004 | Takada et al. |
| 2004/0230309 A1 | 11/2004 | Di Mauro et al. |
| 2004/0236366 A1 | 11/2004 | Kennedy |
| 2004/0247641 A1 | 12/2004 | Felt et al. |
| 2005/0010231 A1 | 1/2005 | Myers |
| 2005/0010297 A1 | 1/2005 | Watson et al. |
| 2005/0015140 A1 | 1/2005 | deBeer |
| 2005/0015148 A1 | 1/2005 | Jansen et al. |
| 2005/0018989 A1 | 1/2005 | Shimizu et al. |
| 2005/0033437 A1 | 2/2005 | Bao et al. |
| 2005/0043733 A1 | 2/2005 | Eisermann et al. |
| 2005/0043808 A1 | 2/2005 | Felt et al. |
| 2005/0049691 A1 | 3/2005 | Mericle et al. |
| 2005/0090901 A1* | 4/2005 | Studer ............ A61F 2/441 623/17.12 |
| 2005/0119662 A1 | 6/2005 | Reiley et al. |
| 2005/0142315 A1 | 6/2005 | DeSimone et al. |
| 2005/0149022 A1 | 7/2005 | Shaolian et al. |
| 2005/0159749 A1 | 7/2005 | Levy et al. |
| 2005/0171604 A1 | 8/2005 | Michalow |
| 2005/0192671 A1 | 9/2005 | Bao et al. |
| 2005/0197711 A1 | 9/2005 | Cachia |
| 2005/0209629 A1 | 9/2005 | Kerr et al. |
| 2005/0228260 A1 | 10/2005 | Burwell et al. |
| 2005/0234453 A1 | 10/2005 | Shaolian et al. |
| 2005/0251140 A1 | 11/2005 | Shaolian et al. |
| 2005/0284485 A9 | 12/2005 | Nelson et al. |
| 2006/0009550 A1 | 1/2006 | Messersmith et al. |
| 2006/0015105 A1 | 1/2006 | Warren et al. |
| 2006/0036253 A1 | 2/2006 | Leroux et al. |
| 2006/0084985 A1 | 4/2006 | Kim et al. |
| 2006/0100547 A1 | 5/2006 | Rabiner et al. |
| 2006/0100635 A1 | 5/2006 | Reiley et al. |
| 2006/0100706 A1 | 5/2006 | Shadduck et al. |
| 2006/0111726 A1 | 5/2006 | Felt et al. |
| 2006/0122625 A1 | 6/2006 | Truckai et al. |
| 2006/0142747 A1 | 6/2006 | Appling |
| 2006/0155296 A1 | 7/2006 | Richter |
| 2006/0173464 A1* | 8/2006 | Ellman ............ A61B 17/8836 606/93 |
| 2006/0183811 A1 | 8/2006 | Melikechi et al. |
| 2006/0184246 A1 | 8/2006 | Zwirkoski |
| 2006/0195165 A1 | 8/2006 | Gertner et al. |
| 2006/0217747 A1 | 9/2006 | Ferree |
| 2006/0229617 A1 | 10/2006 | Meller et al. |
| 2006/0229625 A1 | 10/2006 | Truckai et al. |
| 2006/0247787 A1 | 11/2006 | Rydell et al. |
| 2006/0253102 A1 | 11/2006 | Nance et al. |
| 2006/0253200 A1 | 11/2006 | Bao et al. |
| 2006/0258981 A1 | 11/2006 | Eidenschink |
| 2006/0264950 A1 | 11/2006 | Nelson et al. |
| 2006/0264951 A1 | 11/2006 | Nelson et al. |
| 2006/0264952 A1 | 11/2006 | Nelson et al. |
| 2006/0265077 A1 | 11/2006 | Zwirkoski |
| 2006/0271024 A1 | 11/2006 | Gertner et al. |
| 2006/0271061 A1 | 11/2006 | Beyar et al. |
| 2006/0276793 A1 | 12/2006 | Berry |
| 2006/0276819 A1 | 12/2006 | Osorio et al. |
| 2006/0282169 A1 | 12/2006 | Felt et al. |
| 2006/0287730 A1 | 12/2006 | Segal et al. |
| 2007/0027547 A1 | 2/2007 | Rydell et al. |
| 2007/0067032 A1 | 3/2007 | Felt et al. |
| 2007/0087031 A1 | 4/2007 | Ashman et al. |
| 2007/0100327 A1 | 5/2007 | Smith |
| 2007/0104416 A1 | 5/2007 | Shimizu et al. |
| 2007/0118143 A1 | 5/2007 | Ralph et al. |
| 2007/0123876 A1 | 5/2007 | Czartoski et al. |
| 2007/0123877 A1* | 5/2007 | Goldin ............ A61B 17/7225 606/62 |
| 2007/0123878 A1 | 5/2007 | Shaver et al. |
| 2007/0161991 A1 | 7/2007 | Altarac et al. |
| 2007/0198023 A1 | 8/2007 | Sand et al. |
| 2007/0225705 A1 | 9/2007 | Osario et al. |
| 2007/0233146 A1 | 10/2007 | Henniges et al. |
| 2007/0239148 A1 | 10/2007 | Scheller |
| 2007/0255287 A1 | 11/2007 | Rabiner |
| 2008/0015500 A1 | 1/2008 | Herweck et al. |
| 2008/0019657 A1 | 1/2008 | Maitland et al. |
| 2008/0021474 A1 | 1/2008 | Bonutti et al. |
| 2008/0039854 A1 | 2/2008 | Rabiner |
| 2008/0080205 A1 | 4/2008 | Forrester et al. |
| 2008/0103505 A1* | 5/2008 | Fransen ............ A61B 17/7097 606/92 |
| 2008/0125784 A1 | 5/2008 | Rabiner et al. |
| 2008/0154266 A1 | 6/2008 | Protopsaltis et al. |
| 2008/0154368 A1 | 6/2008 | Justis |
| 2008/0154373 A1 | 6/2008 | Protopsaltis et al. |
| 2008/0183122 A1 | 7/2008 | Fisher et al. |
| 2008/0188805 A1 | 8/2008 | Davies et al. |
| 2008/0188858 A1 | 8/2008 | Luzzi et al. |
| 2008/0234820 A1 | 9/2008 | Felt et al. |
| 2008/0249529 A1 | 10/2008 | Zarda et al. |
| 2008/0255560 A1 | 10/2008 | Myers et al. |
| 2008/0269750 A1 | 10/2008 | Justin |
| 2008/0287951 A1 | 11/2008 | Stoneburger et al. |
| 2008/0308753 A1 | 12/2008 | Stuba et al. |
| 2009/0005782 A1 | 1/2009 | Chirico et al. |
| 2009/0018524 A1 | 1/2009 | Greenhalgh et al. |
| 2009/0024166 A1 | 1/2009 | Carl et al. |
| 2009/0048629 A1 | 2/2009 | Rabiner |
| 2009/0054900 A1 | 2/2009 | Rabiner et al. |
| 2009/0076610 A1 | 3/2009 | Afzal et al. |
| 2009/0093887 A1 | 4/2009 | Walter et al. |
| 2009/0112196 A1 | 4/2009 | Rabiner et al. |
| 2009/0118833 A1 | 5/2009 | Hudgins et al. |
| 2009/0125028 A1 | 5/2009 | Teisen et al. |
| 2009/0171265 A1 | 7/2009 | Doty et al. |
| 2009/0171358 A1 | 7/2009 | Chang et al. |
| 2009/0177204 A1 | 7/2009 | Colleran et al. |
| 2009/0182336 A1 | 7/2009 | Brenzel et al. |
| 2009/0187192 A1 | 7/2009 | Rabiner et al. |
| 2009/0216232 A1 | 8/2009 | Buford, III et al. |
| 2009/0228007 A1 | 9/2009 | Justin et al. |
| 2009/0254064 A1 | 10/2009 | Boatman |
| 2009/0287309 A1 | 11/2009 | Walch et al. |
| 2009/0306589 A1 | 12/2009 | Tilson et al. |
| 2010/0076503 A1 | 3/2010 | Mordechay et al. |
| 2010/0234958 A1 | 9/2010 | Linares |
| 2010/0241178 A1 | 9/2010 | Tilson et al. |
| 2010/0249942 A1 | 9/2010 | Goswami et al. |
| 2010/0256641 A1 | 10/2010 | Rabiner et al. |
| 2010/0262069 A1 | 10/2010 | Rabiner et al. |
| 2010/0262188 A1 | 10/2010 | Rabiner et al. |
| 2010/0265733 A1 | 10/2010 | O'Leary et al. |
| 2010/0318087 A1 | 12/2010 | Scribner et al. |
| 2010/0331850 A1 | 12/2010 | Rabiner |
| 2011/0004213 A1 | 1/2011 | Rabiner et al. |

(56) References Cited

U.S. PATENT DOCUMENTS

| | | |
|---|---|---|
| 2011/0009871 A1 | 1/2011 | Rabiner |
| 2011/0029093 A1 | 2/2011 | Bojarski et al. |
| 2011/0046746 A1 | 2/2011 | Rabiner et al. |
| 2011/0077651 A1 | 3/2011 | Lozier et al. |
| 2011/0082504 A1 | 4/2011 | Singhatt et al. |
| 2011/0098713 A1 | 4/2011 | Rabiner et al. |
| 2011/0110114 A1 | 5/2011 | Papac et al. |
| 2011/0112588 A1 | 5/2011 | Linderman et al. |
| 2011/0118740 A1 | 5/2011 | Rabiner et al. |
| 2011/0137317 A1 | 6/2011 | O'Halloran et al. |
| 2011/0160870 A1 | 6/2011 | Baumgartner et al. |
| 2011/0166306 A1 | 7/2011 | Stansbury et al. |
| 2011/0218826 A1 | 9/2011 | Krinke et al. |
| 2011/0268866 A1 | 11/2011 | Parker |
| 2011/0288522 A1 | 11/2011 | Hollowell et al. |
| 2011/0313356 A1 | 12/2011 | Rabiner et al. |
| 2012/0016371 A1 | 1/2012 | O'Halloran et al. |
| 2012/0022540 A1 | 1/2012 | Chasmawala et al. |
| 2012/0029102 A1 | 2/2012 | Rose et al. |
| 2012/0041557 A1 | 2/2012 | Frigg |
| 2012/0065643 A1 | 3/2012 | Rabiner et al. |
| 2012/0165941 A1 | 6/2012 | Rabiner et al. |
| 2012/0259375 A1 | 10/2012 | Druma et al. |
| 2012/0262939 A1 | 10/2012 | O'Leary et al. |
| 2012/0289968 A1 | 11/2012 | Rabiner |
| 2012/0316652 A1 | 12/2012 | Renganath et al. |
| 2013/0003406 A1 | 1/2013 | O'Leary et al. |
| 2013/0006304 A1 | 1/2013 | Rabiner et al. |
| 2013/0012998 A1 | 1/2013 | Altarac et al. |
| 2013/0013008 A1 | 1/2013 | Rabiner et al. |
| 2013/0013009 A1 | 1/2013 | Colleran et al. |
| 2013/0013010 A1 | 1/2013 | Rabiner et al. |
| 2013/0018482 A1 | 1/2013 | Meridew et al. |
| 2013/0023876 A1 | 1/2013 | Rabiner et al. |
| 2013/0023877 A1 | 1/2013 | Rabiner et al. |
| 2013/0023886 A1 | 1/2013 | Rabiner et al. |
| 2013/0041472 A1 | 2/2013 | Rabiner et al. |
| 2013/0046390 A1 | 2/2013 | Rabiner et al. |
| 2013/0066326 A1 | 3/2013 | Rabiner et al. |
| 2013/0158607 A1 | 6/2013 | Rabiner et al. |
| 2013/0184715 A1 | 7/2013 | Rabiner et al. |
| 2013/0310875 A1 | 11/2013 | Rabiner et al. |
| 2014/0018806 A1 | 1/2014 | DiPoto et al. |
| 2014/0135847 A1 | 5/2014 | Rabiner et al. |
| 2014/0142581 A1 | 5/2014 | Rabiner et al. |
| 2014/0148813 A1 | 5/2014 | Rabiner et al. |
| 2014/0163453 A1 | 6/2014 | Rabiner et al. |
| 2014/0180288 A1 | 6/2014 | Rabiner et al. |
| 2015/0066028 A1 | 3/2015 | Rabiner et al. |
| 2015/0066085 A1 | 3/2015 | Rabiner et al. |
| 2015/0080900 A1 | 3/2015 | Rabiner et al. |
| 2015/0088268 A1 | 3/2015 | Rabiner et al. |
| 2015/0374498 A1 | 12/2015 | Rabiner et al. |
| 2016/0022333 A1 | 1/2016 | Rabiner et al. |
| 2016/0128750 A1 | 5/2016 | Rabiner et al. |
| 2016/0128836 A1 | 5/2016 | Rabiner et al. |
| 2017/0255077 A1 | 9/2017 | DiPoto et al. |
| 2018/0036054 A1 | 2/2018 | Rabiner et al. |
| 2018/0092672 A1 | 4/2018 | Rabiner et al. |
| 2019/0021773 A1 | 1/2019 | Rabiner et al. |
| 2019/0231533 A1 | 8/2019 | Rabiner et al. |

FOREIGN PATENT DOCUMENTS

| | | |
|---|---|---|
| EP | 2 298 201 | 3/2011 |
| JP | 2001-527437 | 12/2001 |
| JP | 2004-526525 | 9/2002 |
| JP | 2005-511143 | 4/2005 |
| JP | 2006-212425 | 8/2006 |
| NL | 9001858 | 3/1992 |
| WO | WO 1998/38918 | 9/1998 |
| WO | WO 1999/043266 | 9/1999 |
| WO | WO 2002/030338 | 4/2002 |
| WO | WO 2002/043628 | 6/2002 |
| WO | WO 2003/047472 | 6/2003 |
| WO | WO 2004/045393 | 6/2004 |
| WO | WO 2004/058045 | 7/2004 |
| WO | WO 2004/073563 | 9/2004 |
| WO | WO 2004/112661 | 12/2004 |
| WO | WO 2005/102224 | 11/2005 |
| WO | WO 2005/112804 | 12/2005 |
| WO | WO 2006/016807 | 2/2006 |
| WO | WO 2007/002251 | 1/2007 |
| WO | WO 2007/059259 | 5/2007 |
| WO | WO 2007/075375 | 7/2007 |
| WO | WO 2007/127255 | 11/2007 |
| WO | WO 2007/127260 | 11/2007 |
| WO | WO 2008/021972 | 2/2008 |
| WO | WO 2008/039811 | 4/2008 |
| WO | WO 2008/063265 | 5/2008 |
| WO | WO 2008/096363 | 8/2008 |
| WO | WO 2009/059090 | 5/2009 |
| WO | WO 2009/064847 | 5/2009 |
| WO | WO 2009/082688 | 7/2009 |
| WO | WO 2009/088927 | 7/2009 |
| WO | WO 2009/091811 | 7/2009 |
| WO | WO 2009/131999 | 10/2009 |
| WO | WO 2010/050965 | 5/2010 |
| WO | WO 2010/118158 | 10/2010 |
| WO | WO 2011/060062 | 5/2011 |
| WO | WO 2011/066522 | 6/2011 |
| WO | WO 2011/071567 | 6/2011 |
| WO | WO 2011/162910 | 12/2011 |
| WO | WO 2012/050583 | 4/2012 |
| WO | WO 2012/051312 | 4/2012 |
| WO | WO 2012/088432 | 6/2012 |
| WO | WO 2013/013069 | 1/2013 |
| WO | WO 2013/013071 | 1/2013 |
| WO | WO 2013/013072 | 1/2013 |
| WO | WO 2013/059609 | 4/2013 |
| WO | WO 2014/011669 | 1/2014 |
| WO | WO 2014/100427 | 6/2014 |

OTHER PUBLICATIONS

USPTO Office Action in U.S. Appl. No. 14/843,286 dated Jun. 7, 2018.
U.S. Appl. No. 11/789,906, published as 2007/0255287, now U.S. Pat. No. 7,811,290, filed Apr. 26, 2007, published Nov. 1, 2007, issued Oct. 12, 2010, Apparatus and Methods for Reinforcing Bone.
U.S. Appl. No. 11/789,907, published as 2008/0039854, now U.S. Pat. No. 7,806,900, filed Apr. 26, 2007, published Feb. 14, 2008, issued Oct. 5, 2010, Apparatus and Methods for Delivery of Reinforcing Materials to Bone.
U.S. Appl. No. 11/903,123, published as 2008/0125784, now U.S. Pat. No. 7,811,284, filed Sep. 20, 2007, published May 29, 2008, issued Oct. 12, 2010, Systems and Methods for Internal Bone Fixation.
U.S. Appl. No. 11/964,370, published as 2010/0256641, now U.S. Pat. No. 8,403,968, filed Dec. 26, 2007, published Oct. 7, 2010, issued Mar. 26, 2013, Apparatus and Methods for Repairing Craniomaxillofacial Bones Using Customized Bone Plates.
U.S. Appl. No. 12/262,370, published as 2009/0112196, now U.S. Pat. No. 9,427,289, filed Oct. 31, 2008, published Apr. 30, 2009, issued Aug. 30, 2016, Light Source.
U.S. Appl. No. 12/262,411, published as 2009/0054900, now U.S. Pat. No. 7,879,041, filed Oct. 31, 2008, published Feb. 26, 2009, issued Feb. 1, 2011, Systems and Methods for Internal Bone Fixation.
U.S. Appl. No. 12/755,105, published as 2010/0265733, now U.S. Pat. No. 8,210,729, filed Apr. 6, 2010, published Oct. 21, 2010, issued Jul. 3, 2012, Attachment System for Light-Conducting Fibers.
U.S. Appl. No. 12/755,784, published as 2010/0262069, now U.S. Pat. No. 8,512,338, filed Apr. 7, 2010, published Oct. 14, 2010, issued Aug. 20, 2013, Photodynamic Bone Stabilization Systems and Methods for Reinforcing Bone.
U.S. Appl. No. 12/756,014, published as 2010/0262188, filed Apr. 7, 2010, published Oct. 14, 2010, Photodynamic Bone Stablization Systems and Methods for Treating Spine Conditions.

(56) References Cited

OTHER PUBLICATIONS

U.S. Appl. No. 12/858,924, published as 2011/0004213, now U.S. Pat. No. 8,366,711, filed Aug. 18, 2010, published Jan. 6, 2011, issued Feb. 5, 2013, Systems and Methods for Internal Bone Fixation.
U.S. Appl. No. 12/859,680, published as 2011/0046746, now U.S. Pat. No. 8,870,965, filed Aug. 19, 2010, published Feb. 24, 2011, issued Oct. 28, 2014, Devices and Methods for Bone Alignment, Stabilization and Distraction.
U.S. Appl. No. 12/875,460, published as 2010/0331850, now U.S. Pat. No. 8,246,628, filed Sep. 3, 2010, published Dec. 30, 2010, issued Aug. 21, 2012, Apparatus for Delivery of Reinforcing Materials to Bone.
U.S. Appl. No. 12/886,288, published as 2011/0009871, now U.S. Pat. No. 8,348,956, filed Sep. 20, 2010, published Jan. 13, 2011, issued Jan. 8, 2013, Apparatus and Methods for Reinforcing Bone.
U.S. Appl. No. 12/943,544, published as 2011/0118740, filed Nov. 10, 2010, published May 19, 2011, Intramedullary Implants Having Variable Fastener Placement.
U.S. Appl. No. 12/983,496, published as 2011/0098713, now U.S. Pat. No. 8,734,460, filed Jan. 3, 2011, published Apr. 28, 2011, issued May 27, 2014, Systems and Methods for Internal Bone Fixation.
U.S. Appl. No. 13/088,916, published as 2011/0313356, now U.S. Pat. No. 8,684,965, filed Apr. 18, 2011, published Dec. 22, 2011, issued Apr. 1, 2014, Photodynamic Bone Stabilization and Drug Delivery Systems.
U.S. Appl. No. 13/335,110, published as 2012/0165941, now U.S. Pat. No. 9,179,959, filed Dec. 22, 2011, published Jun. 28, 2012, issued Nov. 10, 2015, Systems and Methods for Treating Conditions and Diseases of the Spine.
U.S. Appl. No. 13/538,138, published as 2012/0262939, now U.S. Pat. No. 8,328,402, filed Jun. 29, 2012, published Oct. 18, 2012, issued Dec. 11, 2012, Attachment System for Light-Conducting Fibers.
U.S. Appl. No. 13/553,051, published as 2013/0023876, filed Jul. 19, 2012, published Jan. 24, 2013, Combination Photodynamic Devices.
U.S. Appl. No. 13/553,247, published as 2013/0023886, filed Jul. 19, 2012, published Jan. 24, 2013, Devices and Methods for Bone Restructure and Stabilization.
U.S. Appl. No. 13/553,450, published as 2013/0046390, now U.S. Pat. No. 9,144,442, filed Jul. 19, 2012, published Feb. 21, 2013, issued Sep. 29, 2015, Photodynamic Articular Joint Implants and Methods of Use.
U.S. Appl. No. 13/561,249, published as 2012/0289968, now U.S. Pat. No. 8,668,701, filed Jul. 30, 2012, published Nov. 15, 2012, issued Mar. 11, 2014, Apparatus for Delivery of Reinforcing Materials to Bone.
U.S. Appl. No. 13/613,982, published as 2013/0003406, now U.S. Pat. No. 8,936,382, filed Sep. 13, 2012, published Jan. 3, 2013, issued Jan. 20, 2015, Attachment System for Light-Conducting Fibers.
U.S. Appl. No. 13/616,416, published as 2013/0023877, now U.S. Pat. No. 8,574,233, filed Sep. 14, 2012, published Jan. 24, 2013, issued Nov. 5, 2013, Photodynamic Bone Stabilization Systems and Methods for Reinforcing Bone.
U.S. Appl. No. 13/616,781, published as 2013/0066326, now U.S. Pat. No. 8,906,030, filed Sep. 14, 2012, published Mar. 14, 2013, issued Dec. 9, 2014, Systems and Methods for Internal Bone Fixation.
U.S. Appl. No. 13/617,058, published as 2013/0006304, filed Sep. 14, 2012, published Jan. 3, 2013, Photodynamic Bone Stabilization Systems and Methods for Treating Spine Conditions.
U.S. Appl. No. 13/617,181, published as 2013/0013008, now U.S. Pat. No. 8,915,966, filed Sep. 14, 2012, published Jan. 10, 2013, issued Dec. 23, 2014, Devices and Methods for Bone Alignment, Stabilization and Distraction.
U.S. Appl. No. 13/617,557, published as 2013/0013010, filed Sep. 14, 2012, published Jan. 10, 2013, Light Source.

U.S. Appl. No. 13/655,808, published as 2013/0041472, now U.S. Pat. No. 8,936,644, filed Oct. 19, 2012, published Feb. 14, 2013, issued Jan. 20, 2015, Systems and Methods for Joint Stabilization.
U.S. Appl. No. 13/730,521, published as 2013/0184715, now U.S. Pat. No. 8,906,031, filed Dec. 28, 2012, published Jul. 18, 2013, issued Dec. 9, 2014, Systems and Methods for Internal Bone Fixation.
U.S. Appl. No. 13/772,947, published as 2013/0158607, now U.S. Pat. No. 8,672,982, filed Feb. 21, 2013, published Jun. 20, 2013, issued Mar. 18, 2014, Apparatus and Methods for Repairing Craniomaxillofacial Bones Using Customized Bone Plates.
U.S. Appl. No. 13/796,085, published as 2014/0180288, now U.S. Pat. No. 9,687,281, filed Mar. 12, 2013, published Jun. 26, 2014, issued Jun. 27, 2017, Distal Tip for Bone Fixation Devices.
U.S. Appl. No. 13/800,518, published as 2014/0018806, now U.S. Pat. No. 8,939,977, filed Mar. 13, 2013, published Jan. 16, 2014, issued Jan. 27, 2015, Systems and Methods for Separating Bone Fixation Devices from Introducer.
U.S. Appl. No. 13/952,905, published as 2013/0310875, now U.S. Pat. No. 9,050,079, filed Jul. 29, 2013, published Nov. 21, 2013, issued Jun. 9, 2015, Apparatus and Methods for Attaching Soft Tissue to Bone.
U.S. Appl. No. 14/163,027, published as 2014/0135847, now U.S. Pat. No. 9,005,254, filed Jan. 24, 2014, published May 15, 2014, issued Apr. 14, 2015, Methods for Repairing Craniomaxillofacial Bones Using Customized Bone Plates.
U.S. Appl. No. 14/164,846, published as 2014/0142581, now U.S. Pat. No. 9,265,549, filed Jan. 27, 2014, published May 22, 2014, issued Feb. 23, 2016, Apparatus for Delivery of Reinforcing Materials to Bone.
U.S. Appl. No. 14/171,036, published as 2014/0148813, now U.S. Pat. No. 9,254,156, filed Feb. 3, 2014, published May 29, 2014, issued Feb. 9, 2016, Apparatus for Delivery of Reinforcing Materials to Bone.
U.S. Appl. No. 14/177,748, published as 2014/0163453, filed Feb. 11, 2014, published Jun. 12, 2014, Photodynamic Bone Stabilization and Drug Delivery Systems.
U.S. Appl. No. 14/535,913, published as 2015/0066085, now U.S. Pat. No. 9,717,542, filed Nov. 7, 2014, published Mar. 5, 2015, issued Aug. 1, 2017, Systems and Methods for Internal Bone Fixation.
U.S. Appl. No. 14/535,971, published as 2015/0066028, now U.S. Pat. No. 9,433,450, filed Nov. 7, 2014, published Mar. 5, 2015, issued Sep. 6, 2016, Systems and Methods for Internal Bone Fixation.
U.S. Appl. No. 14/550,051, published as 2015/0088268, now U.S. Pat. No. 9,254,195, filed Nov. 21, 2014, published Mar. 26, 2015, issued Feb. 9, 2016, Systems and Methods for Joint Stabilization.
U.S. Appl. No. 14/551,650, published as 2015/0080900, now U.S. Pat. No. 9,125,706, filed Nov. 24, 2014, published Mar. 19, 2015, issued Sep. 8, 2015, Devices and Methods for Bone Alignment, Stabilization and Distraction.
U.S. Appl. No. 14/843,286, published as 2015/0374498, filed Sep. 2, 2015, published Dec. 31, 2015, Photodynamic Articular Joint Implants and Methods of Use.
U.S. Appl. No. 14/874,946, published as 2016/0022333, filed Oct. 5, 2015, published Jan. 28, 2016, Systems and Methods for Treating Conditions and Diseases of the Spine.
U.S. Appl. No. 14/988,058, published as 2016/0128836, filed Jan. 5, 2016, published May 12, 2016, Systems and Methods for Joint Stabilization.
U.S. Appl. No. 14/996,275, published as 2016/0128750, now U.S. Pat. No. 9,724,147, filed Jan. 15, 2016, published May 12, 2016, issued Aug. 8, 2017, Apparatus for Delivery of Reinforcing Materials to Bone.
U.S. Appl. No. 15/603,771, filed May 24, 2017, Distal Tip for Bone Fixation Devices.
U.S. Appl. No. 15/655,326, filed Jul. 20, 2017, Apparatus for Delivery of Reinforcing Materials to Bone.
Jovanovic et al., "Fixion Nails for Humeral Fractures, Injury", Int. J. Care Injured, vol. 35, Issue 11, pp. 1140-1142, Nov. 2004.
Maruyama et al., "Metacarpal Fracture Fixation with Absorbable Polyglycolide Rods and Stainless Steel K Wires: A Biomechanical

(56) References Cited

OTHER PUBLICATIONS

Comparison", Journal of Biomedical Materials Research (Applied Biomaterials), vol. 33, Issue 1, pp. 9-12, Apr. 1996.
Waris et al., "Bioabsorbable Miniplating Versus Metallic Fixation for Metacarpal Fractures", Clinical Orthopaedics and Related Research, No. 410, pp. 310-319, May 2003.
Waris et al., "Self-Reinforced Bioabsorbable Versus Metallic Fixation Systems for Metacarpal and Phalangeal Fractures: A Biomechanical Study", The Journal of Hand Surgery, vol. 27A, No. 5, pp. 902-909, Sep. 2002.
PCT International Search Report based on PCT/US07/20402 dated Apr. 1, 2008.
PCT International Search Report based on PCT/US07/10050 dated Apr. 17, 2008.
PCT International Search Report based on PCT/US07/10038 dated Aug. 27, 2008.
PCT International Search Report based on PCT/US08/81929 dated Jan. 12, 2009.
PCT International Search Report based on PCT/US08/81924 dated Feb. 9, 2009.
PCT International Search Report based on PCT/US08/87630 dated Feb. 24, 2009.
USPTO Office Action in U.S. Appl. No. 11/789,906 dated Apr. 29, 2009.
USPTO Office Action in U.S. Appl. No. 11/789,906 dated Mar. 11, 2010.
USPTO Office Action in U.S. Appl. No. 11/789,906 dated Apr. 30, 2010.
USPTO Office Action in U.S. Appl. No. 11/789,907 dated May 11, 2010.
USPTO Office Action in U.S. Appl. No. 11/903,123 dated Jul. 1, 2010.
PCT International Search Report based on PCT/US10/30275 dated Aug. 11, 2010.
USPTO Office Action in U.S. Appl. No. 12/262,411 dated Sep. 1, 2010.
USPTO Office Action in U.S. Appl. No. 11/964,370 dated Dec. 9, 2010.
PCT International Search Report based on PCT/US10/56219 dated Jan. 20, 2011.
PCT International Search Report based on PCT/US10/46003 dated May 24, 2011.
PCT International Search Report based on PCT/US11/38389 dated Sep. 22, 2011.
USPTO Office Action in U.S. Appl. No. 11/964,370 dated Apr. 28, 2011.
USPTO Office Action in U.S. Appl. No. 11/964,370 dated Sep. 23, 2011.
USPTO Office Action in U.S. Appl. No. 12/858,924 dated Oct. 24, 2011.
USPTO Office Action in U.S. Appl. No. 12/755,784 dated Dec. 23, 2011.
USPTO Office Action in U.S. Appl. No. 12/886,288 dated Dec. 27, 2011.
USPTO Office Action in U.S. Appl. No. 12/875,460 dated Mar. 8, 2012.
USPTO Office Action in U.S. Appl. No. 11/964,370 dated Mar. 16, 2012.
USPTO Office Action in U.S. Appl. No. 12/858,924 dated Apr. 4, 2012.
PCT International Search Report based on PCT/US11/66871 dated May 1, 2012.
USPTO Office Action in U.S. Appl. No. 12/756,014 dated May 11, 2012.
USPTO Office Action in U.S. Appl. No. 12/262,370 dated May 29, 2012.
USPTO Office Action in U.S. Appl. No. 12/943,544 dated Jun. 8, 2012.
USPTO Office Action in U.S. Appl. No. 12/886,288 dated Jun. 26, 2012.
USPTO Office Action in U.S. Appl. No. 11/964,370 dated Jul. 6, 2012.
Extended European Search Report based on EP 07 75 6022 dated Jul. 19, 2012.
Extended European Search Report based on EP 07 75 6016 dated Jul. 18, 2012.
USPTO Office Action in U.S. Appl. No. 12/755,784 dated Aug. 1, 2012.
USPTO Office Action in U.S. Appl. No. 12/858,924 dated Aug. 2, 2012.
USPTO Office Action in U.S. Appl. No. 12/886,288 dated Aug. 15, 2012.
PCT International Search Report based on PCT/US12/47447 dated Oct. 2, 2012.
PCT International Search Report based on PCT/US12/47446 dated Oct. 15, 2012.
PCT International Search Report based on PCT/US12/47444 dated Oct. 18, 2012.
USPTO Office Action in U.S. Appl. No. 12/756,014 dated Oct. 25, 2012.
USPTO Office Action in U.S. Appl. No. 12/859,680 dated Nov. 9, 2012.
USPTO Office Action in U.S. Appl. No. 12/943,544 dated Dec. 3, 2012.
USPTO Office Action in U.S. Appl. No. 12/262,370 dated Dec. 14, 2012.
International Search Report and Written Opinion for PCT/US2012/061047 dated Jan. 7, 2013.
USPTO Office Action in U.S. Appl. No. 12/859,680 dated Jan. 17, 2013.
USPTO Office Action in U.S. Appl. No. 12/756,014 dated Jan. 22, 2013.
USPTO Office Action in U.S. Appl. No. 13/088,916 dated Jan. 23, 2013.
USPTO Office Action in U.S. Appl. No. 13/617,557 dated Feb. 4, 2013.
USPTO Office Action in U.S. Appl. No. 12/755,784 dated Mar. 13, 2013.
USPTO Office Action in U.S. Appl. No. 13/616,416 dated Mar. 25, 2013.
USPTO Office Action in U.S. Appl. No. 13/561,249 dated Apr. 23, 2013.
USPTO Office Action in U.S. Appl. No. 12/262,370 dated Apr. 26, 2013.
USPTO Office Action in U.S. Appl. No. 13/088,916 dated May 13, 2013.
Supplemental European Search Report based on EP 08 87 7881 dated May 15, 2013.
USPTO Office Action in U.S. Appl. No. 13/772,947 dated Jun. 19, 2013.
USPTO Office Action in U.S. Appl. No. 12/859,680 dated Jul. 9, 2013.
USPTO Office Action in U.S. Appl. No. 13/561,249 dated Sep. 16, 2013.
USPTO Office Action in U.S. Appl. No. 13/088,916 dated Sep. 17, 2013.
USPTO Office Action in U.S. Appl. No. 12/943,544 dated Sep. 25, 2013.
PCT International Search Report based on PCT/US13/049773 dated Oct. 1, 2013.
USPTO Office Action in U.S. Appl. No. 13/617,557 dated Oct. 9, 2013.
Extended European Search Report based on EP 10 76 2390 dated Oct. 30, 2013.
USPTO Office Action in U.S. Appl. No. 12/262,370 dated Nov. 21, 2013.
USPTO Office Action in U.S. Appl. No. 12/983,496 dated Feb. 5, 2014.
USPTO Office Action in U.S. Appl. No. 12/756,014 dated Feb. 13, 2014.
USPTO Office Action in U.S. Appl. No. 13/617,181 dated Feb. 25, 2014.

(56) References Cited

OTHER PUBLICATIONS

PCT International Search Report based on PCT/US13/076598 dated Mar. 19, 2014.
USPTO Office Action in U.S. Appl. No. 13/655,808 dated Mar. 27, 2014.
USPTO Office Action in U.S. Appl. No. 13/553,247 dated May 7, 2014.
Extended European Search Report based on EP 14156473 dated May 13, 2014.
USPTO Office Action in U.S. Appl. No. 13/800,518 dated Jun. 10, 2014.
USPTO Office Action in U.S. Appl. No. 12/262,370 dated Jun. 26, 2014.
USPTO Office Action in U.S. Appl. No. 13/617,557 dated Jun. 27, 2014.
USPTO Office Action in U.S. Appl. No. 13/335,110 dated Jul. 31, 2014.
USPTO Office Action in U.S. Appl. No. 13/616,781 dated Aug. 26, 2014.
USPTO Office Action in U.S. Appl. No. 13/730,521 dated Sep. 8, 2014.
USPTO Office Action in U.S. Appl. No. 12/756,014 dated Oct. 7, 2014.
USPTO Office Action in U.S. Appl. No. 13/553,450 dated Oct. 24, 2014.
USPTO Office Action in U.S. Appl. No. 13/335,110 dated Oct. 24, 2014.
USPTO Office Action in U.S. Appl. No. 13/553,247 dated Dec. 5, 2014.
USPTO Office Action in U.S. Appl. No. 13/553,051 dated Dec. 23, 2014.
USPTO Office Action in U.S. Appl. No. 12/262,370 dated Jan. 14, 2015.
USPTO Office Action in U.S. Appl. No. 13/617,557 dated Jan. 15, 2015.
USPTO Office Action in U.S. Appl. No. 13/335,110 dated Feb. 9, 2015.
USPTO Office Action in U.S. Appl. No. 13/796,085 dated Feb. 12, 2015.
USPTO Office Action in U.S. Appl. No. 13/553,051 dated Mar. 31, 2015.
USPTO Office Action in U.S. Appl. No. 13/553,247 dated May 1, 2015.
USPTO Office Action in U.S. Appl. No. 13/297,097 dated May 29, 2015.
USPTO Office Action in U.S. Appl. No. 14/171,036 dated Jun. 1, 2015.
USPTO Office Action in U.S. Appl. No. 14/164,846 dated Jun. 4, 2015.
USPTO Office Action in U.S. Appl. No. 13/617,557 dated Jul. 15, 2015.
USPTO Office Action in U.S. Appl. No. 13/796,085 dated Jul. 17, 2015.
USPTO Office Action in U.S. Appl. No. 13/553,051 dated Sep. 11, 2015.
USPTO Office Action in U.S. Appl. No. 13/553,247 dated Sep. 23, 2015.
USPTO Office Action in U.S. Appl. No. 14/164,846 dated Oct. 14, 2015.
USPTO Office Action in U.S. Appl. No. 14/171,036 dated Oct. 15, 2015.
USPTO Office Action in U.S. Appl. No. 12/262,370 dated Oct. 22, 2015.
USPTO Office Action in U.S. Appl. No. 13/796,085 dated Nov. 27, 2015.
USPTO Office Action in U.S. Appl. No. 13/553,051 dated Jan. 6, 2016.
USPTO Office Action in U.S. Appl. No. 13/617,557 dated Jan. 14, 2016.
USPTO Office Action in U.S. Appl. No. 14/177,748 dated Jan. 25, 2016.
USPTO Office Action in U.S. Appl. No. 14/535,913 dated Feb. 22, 2016.
USPTO Office Action in U.S. Appl. No. 13/553,247 dated Mar. 2, 2016.
USPTO Office Action in U.S. Appl. No. 14/535,971 dated Mar. 4, 2016.
USPTO Office Action in U.S. Appl. No. 12/262,370 dated Jun. 2, 2016.
USPTO Office Action in U.S. Appl. No. 13/796,085 dated Jul. 1, 2016.
USPTO Office Action in U.S. Appl. No. 14/535,913 dated Sep. 26, 2016.
USPTO Office Action in U.S. Appl. No. 13/553,247 dated Oct. 13, 2016.
USPTO Office Action in U.S. Appl. No. 13/996,275 dated Nov. 14, 2016.
PCT International Search Report based on PCT/US2016/60603 dated Jan. 30, 2017.
USPTO Office Action in U.S. Appl. No. 14/874,946 dated May 17, 2017.
USPTO Office Action in U.S. Appl. No. 14/988,058 dated Jun. 12, 2017.
USPTO Office Action in U.S. Appl. No. 15/655,326 dated Aug. 7, 2018.
USPTO Office Action in U.S. Appl. No. 15/603,771 dated Nov. 13, 2018.
USPTO Office Action in U.S. Appl. No. 15/655,326 dated Jan. 30, 2019.
USPTO Office Action in U.S. Appl. No. 15/603,771 dated Jun. 25, 2019.

* cited by examiner

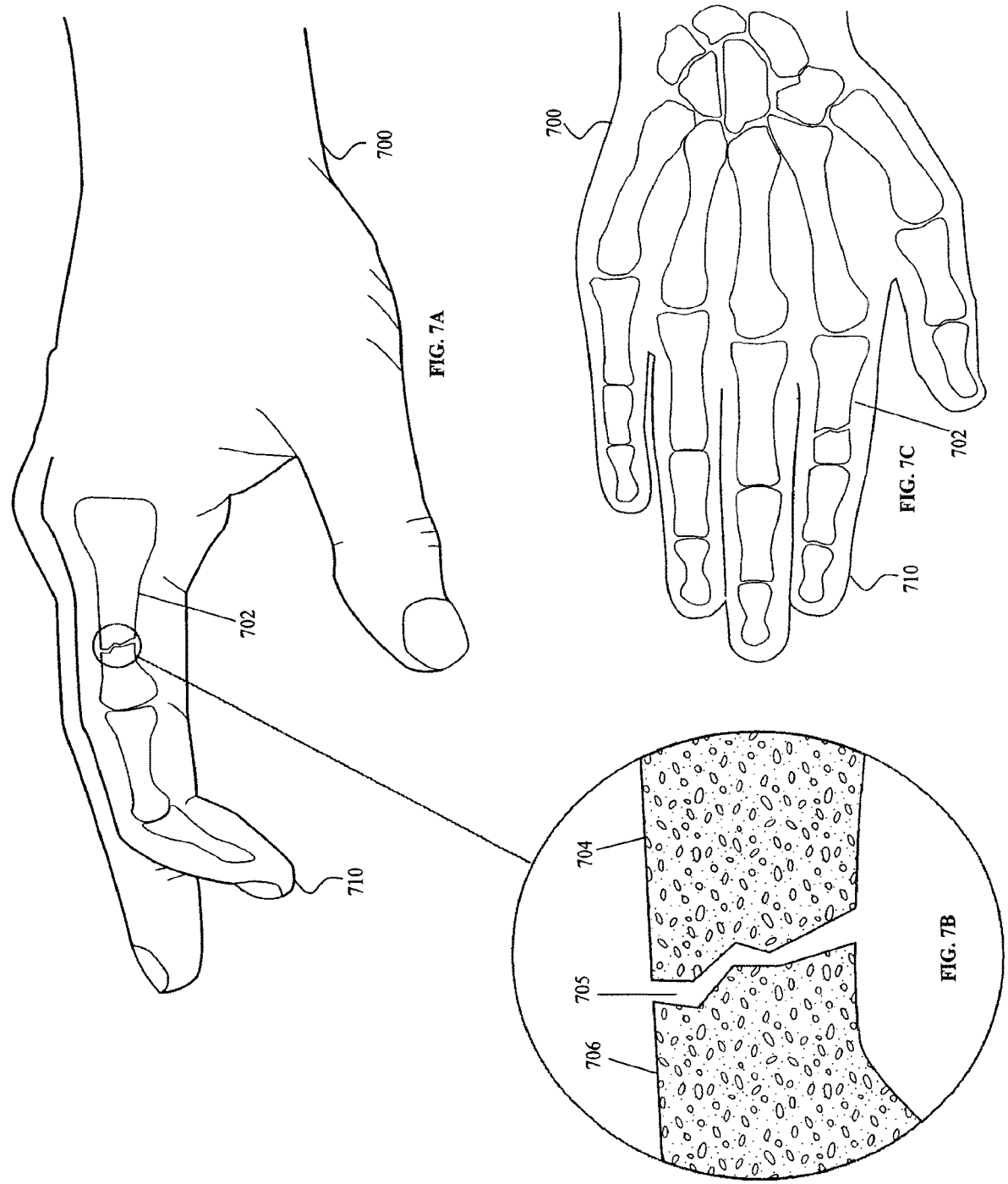

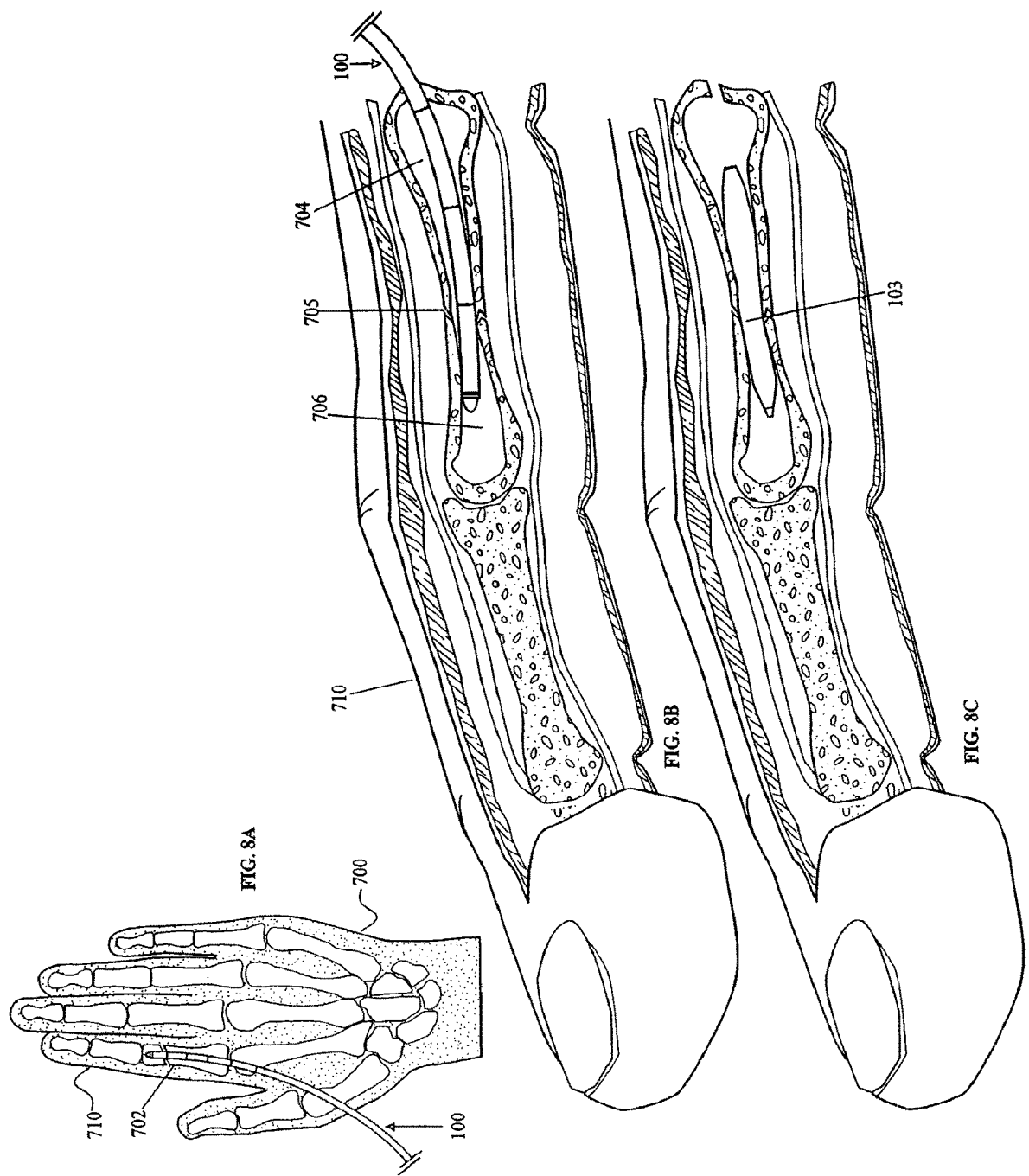

SYSTEMS AND METHODS FOR INTERNAL BONE FIXATION

RELATED APPLICATIONS

This application is a continuation of U.S. application Ser. No. 14/535,913, filed Nov. 7, 2014, now U.S. Pat. No. 9,717,542, which is a continuation of U.S. application Ser. No. 13/730,521, filed on Dec. 28, 2012, now U.S. Pat. No. 8,906,031, which is a continuation of U.S. application Ser. No. 12/858,924, filed on Aug. 18, 2010, now U.S. Pat. No. 8,366,711, which is a continuation of U.S. application Ser. No. 11/903,123, filed on Sep. 20, 2007, now U.S. Pat. No. 7,811,284, which claims the benefit of U.S. Provisional Application Ser. No. 60/858,202, filed Nov. 10, 2006 and U.S. Provisional Application Ser. No. 60/880,646, filed Jan. 16, 2007, and the entirety of these applications are hereby incorporated herein by reference for the teachings therein.

FIELD

The embodiments disclosed herein relate to medical devices for use in repairing a weakened or fractured bone, and more particularly to internal bone fixation devices and methods of using these devices for repairing a weakened or fractured bone.

BACKGROUND

Fracture repair is the process of rejoining and realigning the ends of broken bones. Fracture repair is required when there is a need for restoration of the normal position and function of the broken bone. Throughout the stages of fracture healing, the bones must be held firmly in the correct position and supported until it is strong enough to bear weight. In the event the fracture is not properly repaired, malalignment of the bone may occur, resulting in possible physical dysfunction of the bone or joint of that region of the body.

Until the last century, physicians relied on casts and splints to support the bone from outside the body (external fixation). However, the development of sterile surgery reduced the risk of infection so that doctors could work directly with the bone and could implant materials in the body. Currently there are several internal approaches to repair, strengthen and support a fractured bone. They include the use of internal fixation devices, such as wires, plates, rods, pins, nails, and screws to support the bone directly, and the addition of bone cement mixtures, or bone void fillers to a fractured bone.

The addition of bone cements to a fractured bone for repairing bone and, for example, joining bones are well known in the art. Conventional bone cement injection devices have difficulty adjusting or controlling the injection volume or injection rate of the bone cement in real time in reaction to cancellous bone volume and density conditions encountered inside the fractured bone. Conventional bone cements also may cause complications that include the leakage of the bone cement to an area outside of the fractured bone site, which can result in soft tissue damage as well as nerve root pain and compression.

Thus, there is a need in the art for internal bone fixation devices that repair, strengthen and support a fractured bone using minimally invasive techniques, with ease of use, and minimal damage to the bone and supporting tissues.

SUMMARY

Internal bone fixation devices and methods for using the devices for repairing a weakened or fractured bone are disclosed herein. According to aspects illustrated herein, there is provided an internal bone fixation device that includes a conformable member; and at least one reinforcing material contained within the conformable member, wherein the conformable member moves from a deflated state to an inflated state when the at least one reinforcing material is added to the conformable member.

According to aspects illustrated herein, there is provided a device for use in repairing a fractured bone that includes a delivery catheter having an elongated shaft with a proximal end, a distal end, and a longitudinal axis therebetween, wherein the delivery catheter has an inner void for passage of at least one reinforcing material and an inner lumen for passage of a light source; a conformable member releasably engaging the distal end of the delivery catheter, wherein the conformable member moves from a deflated state to an inflated state when the at least one reinforcing material is delivered to the conformable member; and an adapter releasably engaging the proximal end of the delivery catheter for receiving the light source and the at least one reinforcing material.

According to aspects illustrated herein, there is provided a method for repairing a fractured bone that includes gaining access to an inner cavity of the fractured bone; providing a device for use in repairing the fractured bone, the device comprising a conformable member releasably engaging a delivery catheter, wherein the delivery catheter has an inner void for passage of at least one reinforcing material to the conformable member and an inner lumen for passage of a light source to the conformable member; positioning the conformable member spanning at least two bone segments of the fractured bone; inserting a light source into the inner lumen of the device; adding at least one reinforcing material to the inner void of the device; infusing the at least one reinforcing material through the inner void of the delivery catheter to the conformable member, wherein the conformable member moves from an initial deflated state to a final inflated state; activating the light source to harden the at least one reinforcing material in the inflated conformable member; and releasing the hardened conformable member from the delivery catheter.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIG. 2A shows a balloon portion of the device in a deflated state. FIG. 2B shows a balloon portion of the device in an inflated state.

FIG. 3A shows a perspective view of a distal end of the device. FIG. 3B shows a side cross-sectional view taken along line A-A of the device.

FIG. 5A shows a side cross-sectional view of the device. FIG. 5B shows a cross-sectional view of the device.

FIG. 7A, FIG. 7B and FIG. 7C show illustrative embodiments of a fractured metacarpal bone in a finger of a hand.

FIG. 8A, FIG. 8B and FIG. 8C shows a device of the presently disclosed embodiments used for internal bone fixation. FIG. 8A shows the placement of the device at a metacarpal fracture in a hand of a patient. FIG. 8B shows a side view of a balloon portion of the device as the balloon portion is inflated with a reinforcing material to repair the fracture. FIG. 8C shows a side view of the balloon portion at the site of the bone fracture after the balloon portion has been released from the device.

Figure 1:
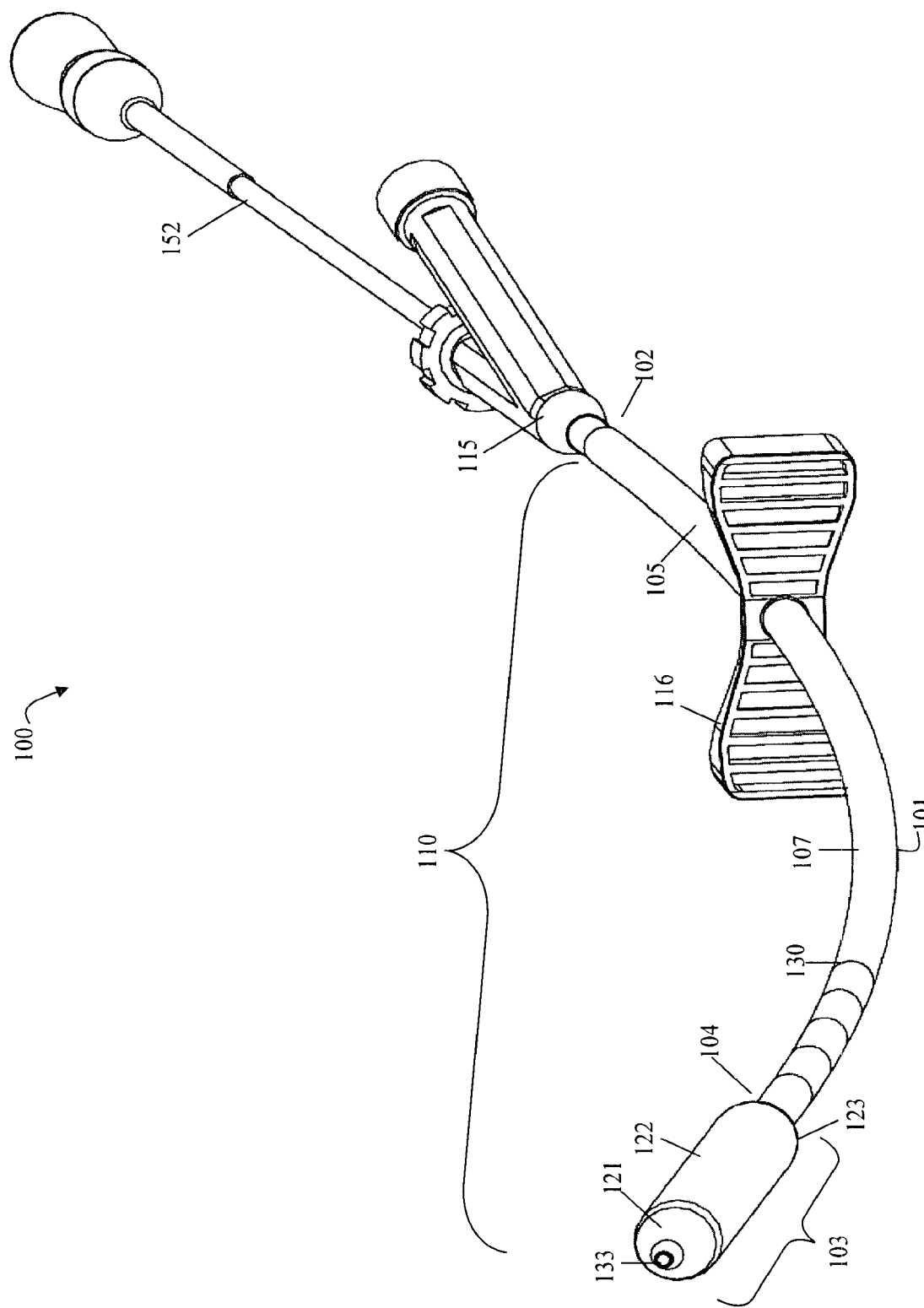
FIG. 1 shows a perspective view of a device for repairing a weakened or fractured bone of the presently disclosed embodiments.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

Medical devices and methods for repairing a weakened or fractured bone are disclosed herein. The devices disclosed herein act as internal bone fixation devices and include a delivery catheter terminating in a releasable conformable member. During a procedure for repairing a fractured bone, the conformable member is placed within an inner cavity of a fractured bone n a deflated state. Once in place, the conformable member is expanded from a deflated state to an inflated state by the addition of at least one reinforcing material. The at least one reinforcing material is subsequently hardened within the conformable member using a light source. The hardened conformable member may then be released from the delivery catheter and sealed to enclose the at least one reinforcing material within the conformable member. The hardened conformable member remains within the inner cavity of the fractured bone and provides support and proper orientation of the fractured bone resulting in the repair, healing, and strengthening of the fractured bone.

Reinforcing materials include, but are not limited to, bone reinforcing mixtures (such as bone cement mixtures, bone void fillers, epoxies, glues and similar adhesives), orthopedic wires, stainless-steel rods, metal pins, and other similar devices. The reinforcing material may be a natural or synthetic material for strengthening, replacing, or reinforcing of bones or bone tissue. Bone reinforcing mixtures include glues, adhesives, cements, hard tissue replacement polymers, biodegradable polymers such as PLA, PGA, and PLA-PGA copolymers, natural coral, hydroxyapatite, beta-tricalcium phosphate, and various other biomaterials known in the art for strengthening, replacing or reinforcing bones. As inert materials, bone reinforcing mixtures may be incorporated into surrounding tissue or gradually replaced by original tissue. Those skilled in the art will recognize that numerous bone reinforcing mixtures known in the art are within the spirit and scope of the presently disclosed embodiments.

A device disclosed herein may be used for the repair of bones that have weakened or fractured due to any of the bone diseases including, but not limited to osteoporosis, achondroplasia, bone cancer, fibrodysplasia ossificans progressiva, fibrous dysplasia, legg calve perthes disease, myeloma, osteogenesis imperfecta, osteomyelitis, osteopenia, osteoporosis, Paget's disease, scoliosis, and other similar diseases. A device disclosed herein may be used for the repair of bones that have weakened or fractured due to an injury, for example, a fall.

Although some of the figures show the fractured bone as a metacarpal bone in the hand, those skilled in the art will recognize that the disclosed devices and methods may be used for repairing other bones including, but not limited to, the femur, tibia, fibula, humerus, ulna, radius, metatarsals, phalanx, phalanges, ribs, spine, vertebrae, clavicle and other bones and still be within the scope and spirit of the disclosed embodiments.

Figure 2A:
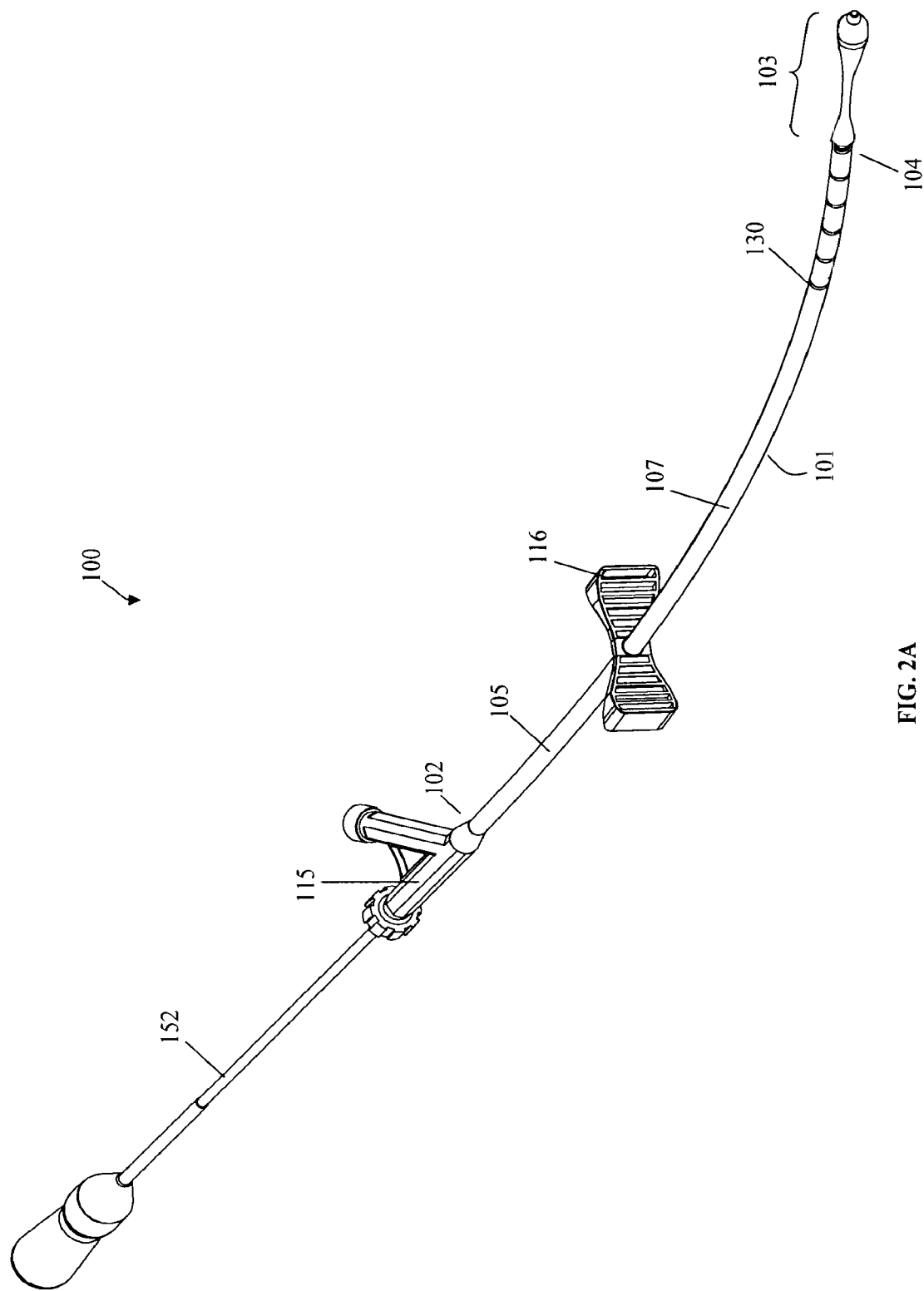
FIG. 2A and FIG. 2B show perspective views of a device for repairing a weakened or fractured bone of the presently disclosed embodiments.
Figure 2B:
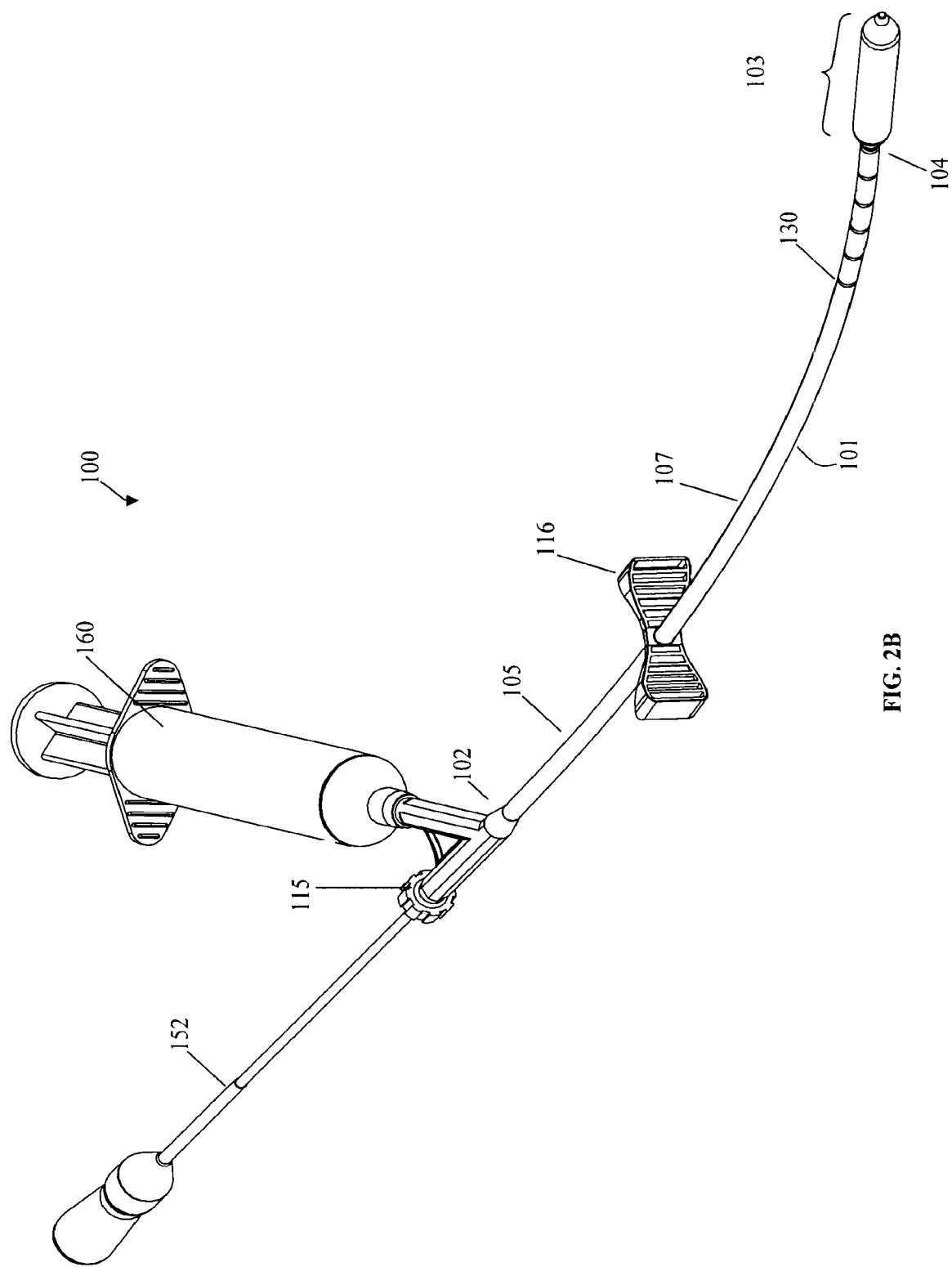

The main components of a device for repairing a weakened or fractured bone are shown generally in FIG. 1 in conjunction with FIG. 2A and FIG. 2B. The device 100 includes a delivery catheter 110 having an elongated shaft 101 with a proximal end 102, a distal end 104, and a longitudinal axis therebetween. In an embodiment, the delivery catheter 110 has a diameter of about 3 mm. The distal end 104 of the delivery catheter 110 terminates in a releasable conformable member 103. In an embodiment, the conformable member is a balloon portion. The balloon portion 103 may move from a deflated state (FIG. 2A) to an inflated state (FIG. 2B) when at least one reinforcing material is delivered to the balloon portion 103. In an embodiment, the balloon portion 103 has a deflated diameter of about 2.5 mm. In an embodiment, the balloon portion 103 has an inflated diameter ranging from about 4 mm to about 9 mm. The reinforcing material may be delivered to the balloon portion 103 via an inner void capable of allowing the reinforcing material to pass through. In an embodiment, a reinforcing material, such as UV-activated glue, is used to inflate and deflate the balloon portion 103. In an embodiment, the balloon portion 103 may be round, flat, cylindrical, oval, rectangular or another shape. The balloon portion 103 may be formed of a pliable, resilient, conformable, and strong material, including but not limited to urethane, polyethylene terephthalate (PET), nylon elastomer and other similar polymers. In an embodiment, the balloon portion 103 is constructed out of a PET nylon aramet or other non-consumable materials. PET is a thermoplastic polymer resin of the polyester family that is used in synthetic fibers. Depending on its processing and thermal history, PET may exist both as an amorphous and as a semi-crystalline material. Semi-crystalline PET has good strength, ductility, stiffness and hardness. Amorphous PET has better ductility, but less stiffness and hardness. PET can be semi-rigid to rigid, depending on its thickness, and is very lightweight. PET is strong and impact-resistant, naturally colorless and transparent and has good resistance to mineral oils, solvents and acids.

In an embodiment, the balloon portion 103 is designed to evenly contact an inner wall of a cavity in a bone. In an embodiment, the balloon portion 103 may have a pre-defined shape to fit inside the cavity in a particularly shaped bone. For example, as depicted in the embodiment of FIG. 1, the pre-defined shape of the balloon portion 103 may be an elongated cylinder. The balloon portion 103 has a proximal end 123, a distal end 121 and a longitudinal axis therebetween having an outer surface 122. In an embodiment, the outer surface 122 of the balloon portion 103 is substantially even and smooth and substantially mates with a wall of the cavity in the bone. In an embodiment, the outer surface 122 of the balloon portion 103 is not entirely smooth and may have some small bumps or convexity/concavity along the length. In some embodiments, there are no major protuberances jutting out from the outer surface 122 of the balloon portion 103. The balloon portion 103 may be designed to remain within the cavity of the bone and not protrude through any holes or cracks in the bone. In an embodiment, the outer surface 122 of the balloon portion 103 may be flush with the wall of the cavity and when the balloon portion 103 is inflated, the outer surface 122 may contact the wall of the cavity along at least a portion of the surface area. In an embodiment, when the balloon portion 103 is inflated, a majority or all of the balloon's 103 outer surface 122 does not contact the wall of the cavity and does not extend through any holes or cracks in the bone.

The outer surface 122 of the balloon portion 103 may be coated with materials such as drugs, bone glue, proteins, growth factors, or other coatings. For example, after a minimally invasive surgical procedure an infection may develop in a patient, requiring the patient to undergo antibiotic treatment. An antibiotic drug may be added to the outer surface 122 of the balloon portion 103 to prevent or combat a possible infection. Proteins, such as, for example, the bone morphogenic protein or other growth factors have been shown to induce the formation of cartilage and bone. A growth factor may be added to the outer surface 122 of the balloon portion 103 to help induce the formation of new bone. Due to the lack of thermal egress of the reinforcing material in the balloon portion 103, the effectiveness and stability of the coating is maintained.

In an embodiment, the outer surface 122 of the balloon portion 103 may have ribs, ridges, bumps or other shapes to help the balloon portion 103 conform to the shape of a bone cavity. Balloons may be constructed to achieve transit within luminal cavities of bones and to expand, manipulate, and remove obstructions. In this way, the balloon portion 103 may slide easier within the luminal bodies without coming in contact with surrounding tissue. The balloon portion 103 may also be designed to be placed in a bone and to grab a fractured bone without any slippage using a textured surface with a variety of shapes such as small ridges or ribs.

In an embodiment, a water soluble glue is applied to the outer surface 122 of the balloon portion 103. When the balloon portion 103 is expanded and engages a moist bone, the water soluble glue on the outer surface 122 of the balloon portion 103 becomes sticky or tacky and acts as a gripping member to increase the conformal bond of the balloon portion 103 to the bone. Once the balloon portion 103 is inflated, the outer surface 122 of the balloon portion 103 grips the bone forming a mechanical bond as well as a chemical bond. These bonds prevent the potential for a bone slippage. The water soluble glue may be cured by any light (e.g., UV not required).

In an embodiment, the balloon portion 103 has a textured surface which provides one or more ridges that allow grabbing all portions of bone fragments of a fractured bone. In an embodiment, ridges are circumferential to the balloon portion 103 and designed to add more grab to the inflated balloon portion 103 on contact with the fractured bone. The ridges are also compressive so the ridges fold up on the fractured bone when the balloon portion 103 is completely inflated. In an embodiment, sand blasted surfacing on the outer surface 122 of the balloon portion 103 improves the connection and adhesion between the outer surface 122 of the balloon portion 103 and the inner bone. The surfacing significantly increases the amount of surface area that comes in contact with the bone resulting in a stronger grip.

The balloon portion 103 of the device 100 typically does not have any valves. One benefit of having no valves is that the balloon portion 103 may be inflated or deflated as much as necessary to assist in the fracture reduction and placement. Another benefit of the balloon portion 103 having no valves is the efficacy and safety of the device 100. Since there is no communication passage of reinforcing material to the body there cannot be any leakage of material because all the material is contained within the balloon portion 103. In an embodiment, a permanent seal is created between the balloon portion 103 that is both hardened and affixed prior to the delivery catheter 110 being removed. The balloon portion 103 may have valves, as all of the embodiments are not intended to be limited in this manner.

The balloon portion 103 of the delivery catheter 110 has a diameter ranging from about 5 mm to about 9 mm. The balloon portion 103 of the delivery catheter 110 has a length ranging from about 20 mm to about 80 mm. In an embodiment, the balloon portion 103 has a diameter of about 5 mm and a length of about 30 mm. In an embodiment, the balloon portion 103 has a diameter of about 5 mm and a length of about 40 mm. In an embodiment, the balloon portion 103 has a diameter of about 6 mm and a length of about 30 mm. In an embodiment, the balloon portion 103 has a diameter of about 6 mm and a length of about 40 mm. In an embodiment, the balloon portion 103 has a diameter of about 6 mm and a length of about 50 mm. In an embodiment, the balloon portion 103 has a diameter of about 7 mm and a length of about 30 mm. In an embodiment, the balloon portion 103 has a diameter of about 7 mm and a length of about 40 mm. In an embodiment, the balloon portion 103 has a diameter of about 7 mm and a length of about 50 mm.

A stiffening member 105 surrounds the elongated shaft 101 of the delivery catheter 110 and provides rigidity over the elongated shaft 101. A pusher or stabilizer 116 is loaded proximal to the balloon portion 103. A slip sleeve 107 surrounds the stiffening member 105. In an embodiment, the slip sleeve 107 surrounds the stiffening member 105 from the proximal end 123 of the balloon portion 103 up until the pusher 116. One or more radiopaque markers or bands 130 may be placed at various locations along the balloon portion 103 and/or the slip sleeve 107. A radiopaque ink bead 133 may be placed at the distal end 121 of the balloon portion 103 for alignment of the device 100 during fluoroscopy. The one or more radiopaque bands 130, using radiopaque materials such as barium sulfate, tantalum, or other materials known to increase radiopacity, allows a medical professional to view the device 100 using fluoroscopy techniques. The one or more radiopaque bands 130 also provide visibility during inflation of the balloon portion 103 to determine the precise positioning of the balloon portion 103 and the device 100 during placement and inflation. The one or more radiopaque bands 130 permit visualization of any voids that may be created by air that gets entrapped in the balloon portion 103. The one or more radiopaque bands 130 permit visualization to preclude the balloon portion 103 from misengaging or not meeting the bone due to improper inflation to maintain a uniform balloon/bone interface.

In an embodiment, an adapter 115, such as a Tuohy-Borst adapter, engages the proximal end 102 of the delivery catheter 110. A light source that includes a light pipe 152 may be introduced into one of the side-arms of the adapter 115 and passes within an inner lumen of the delivery catheter 110 up until the distal end 104 of the delivery catheter 110. An adhesive system housing the reinforcing material may be introduced into another side-arm of the adapter 115, as shown in FIG. 2B. Alternately, a Luer fitting may engage the proximal end 102 of the delivery catheter 110 and a Luer fitting would exist on the light source such that the delivery catheter 110 and the light source would lock together.

Examples of adhesive systems include, but are not limited to, caulking gun type systems, syringe systems, bag systems that contain the bone reinforcing material where the delivery of the bone reinforcing material is controlled using a tube clamp or any other restrictor valve. In the embodiment shown in FIG. 2B, the adhesive system is a syringe 160. In an embodiment, the syringe 160 has a control mechanism that regulates the flow of the reinforcing material. The control mechanism of the syringe 160 allows the reinforcing material to flow into the delivery catheter 110 and the flow may be stopped if desired. The syringe 160 makes direct contact to control the directional flow of the reinforcing material, and the direction of flow of the reinforcing material instantaneously changes within the delivery catheter 110 in response to a change in the direction of the syringe 160.

In an embodiment, the syringe 160 is opaque and does not allow light to penetrate within the syringe 160. Having an opaque syringe 160 ensures that the reinforcing material contained in the syringe 160 is not exposed to light and will not cure in the syringe 160. The reinforcing material is of a liquid consistency, as measured in Centipoise (cP), the unit of dynamic viscosity, so the reinforcing material may be infused from the syringe 160 into the delivery catheter 110 and into the balloon portion 103. Because the reinforcing material has a liquid consistency and is viscous, the reinforcing material may be delivered using low pressure delivery and high pressure delivery is not required, but may be used.

In an embodiment, a separation area is located at the junction between the distal end 123 of the balloon portion 103 and the elongated shaft 101. The separation area may also include an illumination band. When activated, the illumination band causes light to cure the reinforcing material located in the balloon portion 103 within the illumination band. The illumination band extends around the delivery catheter 110 and has a stress concentrator. The stress concentrator may be a notch, groove, channel or similar structure that concentrates stress in the illumination band. The stress concentrator of the illumination band may be notched, scored, indented, pre-weakened or pre-stressed to direct separation of the balloon portion 103 from the elongated shaft 101 of the delivery catheter 110 under specific torsional load. The separation area ensures that there are no leaks of reinforcing material from the elongated shaft of the delivery catheter and/or the balloon portion. The separation area seals the balloon portion and removes the elongated shaft of the delivery catheter by making a break at a known or predetermined site (e.g., a separation area). The separation area may be various lengths and up to about an inch long. When torque (twisting) is applied to the delivery catheter 110, the elongated shaft 101 separates from the balloon portion 103. The twisting creates a sufficient shear to break the residual reinforcing material and create a clean separation of the balloon/shaft interface. The illumination band may be connected to the light source and may be activated by a separate switch. Having a distinct switch to activate the illumination band may help to prevent inadvertent delivery of light from the light source to cure the reinforcing material. The activation of the illumination band seals the balloon portion and seals the end of the delivery catheter, and ensures that there is a "hard seal" of the reinforcing material at the illumination band allowing no reinforcing material to leak from the balloon portion or the delivery catheter.

Figure 3A:
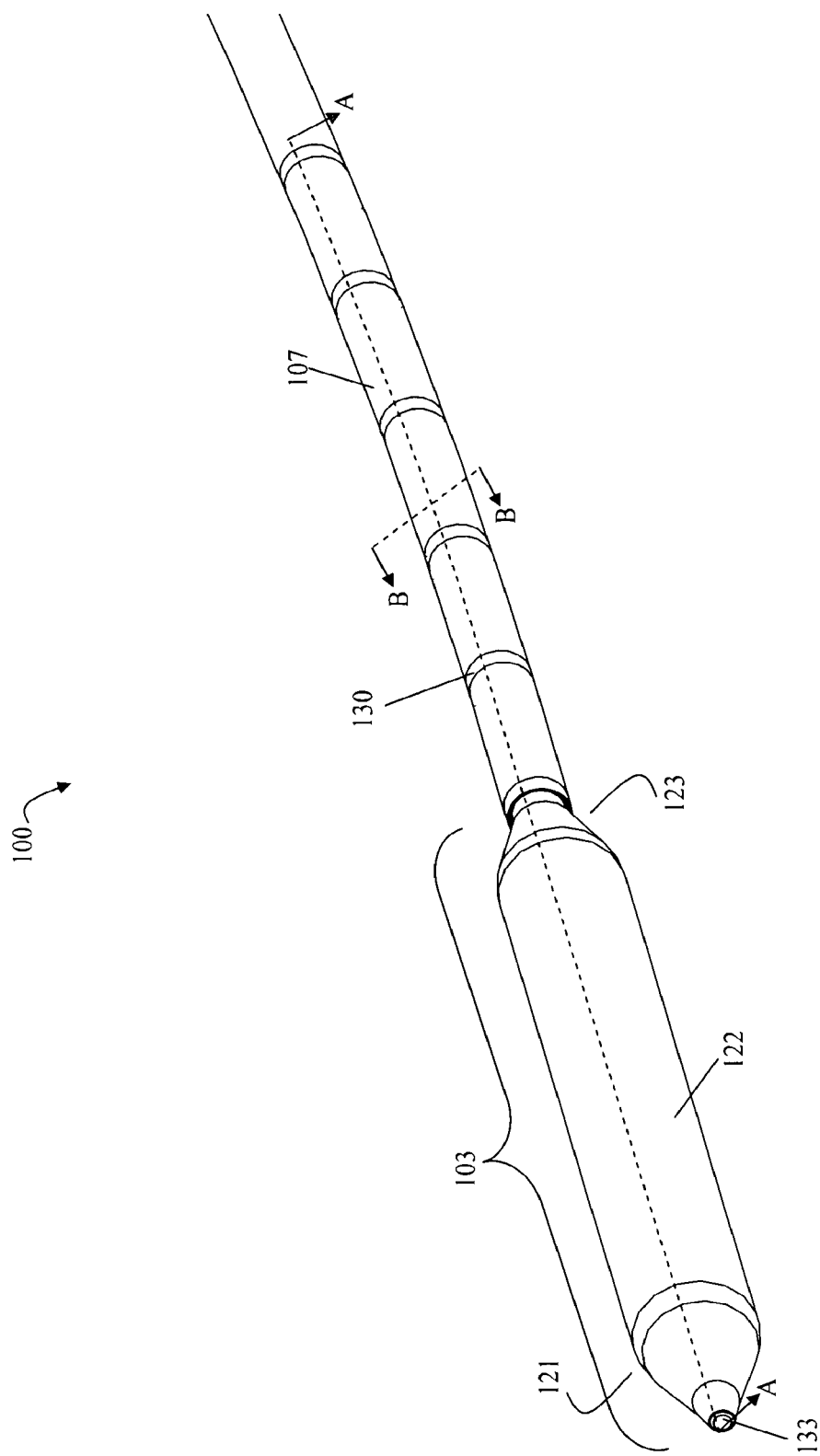
FIG. 3A and FIG. 3B show close-up views of some of the main components of a device for repairing a weakened or fractured bone of the presently disclosed embodiments.
Figure 3B:
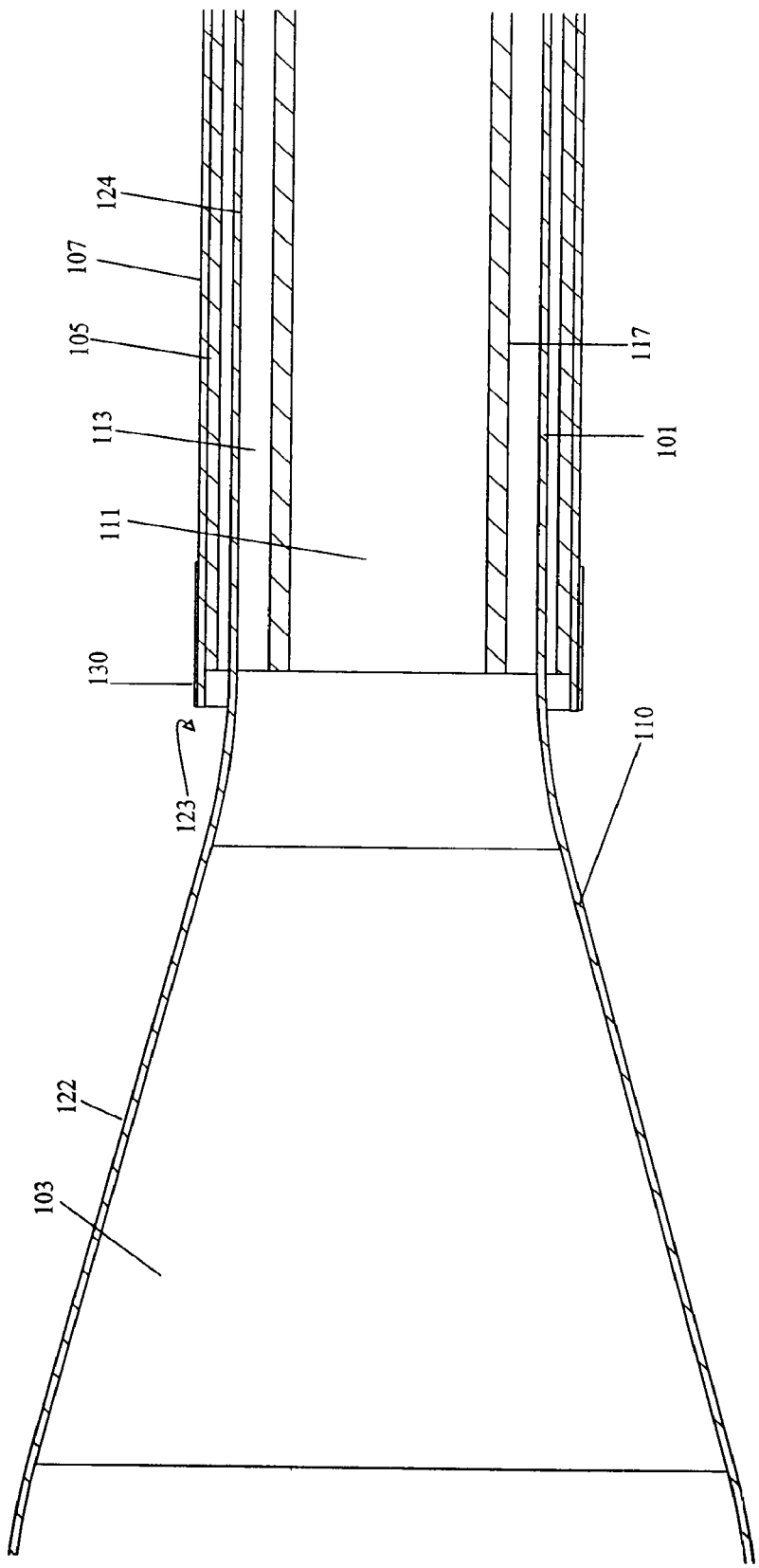

FIG. 3A and FIG. 3B show close-up views of some of the main components of the device 100. One or more radiopaque markers or bands 130 are placed at various locations along the slip sleeve 107 of the device 100. Those skilled in the art will recognize that radiopaque markers 130 may also be placed at various locations along the balloon portion 103. In an embodiment, the one or more radiopaque bands 130 are placed at intervals of about 10 mm along the length of the slip sleeve 107. In an embodiment, a radiopaque ink bead 133 is placed at the distal end 121 of the balloon portion 103 for easy visualization and alignment of the device 100 by fluoroscopy during a repair procedure. The radiopaque markers 130 and radiopaque ink bead 133 are formed using radiopaque material such as barium sulfate, tantalum, or other materials known to increase radiopacity. The radiopaque markers 130 provide visibility during inflation of the balloon portion 103 to determine the precise positioning of the balloon portion 103 and the delivery catheter 110 during placement and inflation. The radiopaque markers 130 permit visualization of voids created by air that may be entrapped in the balloon portion 103. The radiopaque markers 130 permit visualization to preclude the balloon portion 103 from misengaging or not meeting the surface of a bone due to improper inflation. Once the correct positioning of the balloon portion 103 and delivery catheter 110 are determined, the proximal end of the delivery catheter 110 may be attached to a delivery system that contains a reinforcing mixture.

A cross-sectional view taken along line A-A of FIG. 3A is shown in FIG. 3B. As shown in FIG. 3B, the elongated shaft 101 of the delivery catheter 110 terminates in the balloon portion 103 having the outer surface 122. Within the elongated shaft 101 of the delivery catheter 110 is a light pipe conduit 111 for accepting a light source (not shown). A void 113 for passage of a reinforcing material is formed between an inner surface 124 of the delivery catheter 110 and an outer surface 117 of the light pipe conduit 111. A delivery system comprising the reinforcing material may be attached to a side arm of a Tuohy-Borst adapter that is engaged to a proximal end of the delivery catheter 110. The reinforcing material may pass through the void 113 of the delivery catheter 110 and enter the balloon portion 103. The infusion of the reinforcing material causes the balloon portion 103 to inflate to a desired state. In an embodiment, the reinforcing material is infused through the void 113 in the delivery catheter 110 to expand the balloon portion 103 to position a bone in a healing orientation. To establish the healing orientation, the balloon portion 103 inflates until the bones move into an aligned orientation and are supported. Orientation of the bones may be done without any visualization of the process or using x-ray or a fluoroscope. In an embodiment, a C arm imaging system is used as part of a fluoroscope. The C arm imaging system may allow movement or manipulation of the fluoroscope to rotate around tissue while viewing. Other techniques may be used for monitoring or inspecting the expansion of the balloon portion 103 such as magnetic resonance imaging (MRI), ultrasound imaging, x-ray fluoroscopy, Fourier transform infrared spectroscopy, ultraviolet or visible spectroscopy. The balloon portion 103 may be composed of non ferromagnetic materials and, thus, is compatible with MRI.

As shown in FIG. 3B, the outer slip sleeve 107 surrounds the stiffening member 105. The stiffening member 105 surrounds and provides rigidity to the elongated shaft of the delivery catheter 110. The light pipe conduit 111 provides a space for a light source to pass through. The void 113 is formed between the outer surface 117 of the light pipe conduit 111 and the inner surface 124 of the delivery catheter 110. This void 113 provides a passageway for the reinforcing material. The outer surface 117 of the light pipe conduit 111 allows for a separation between the light source and the reinforcing material.

Figure 4:
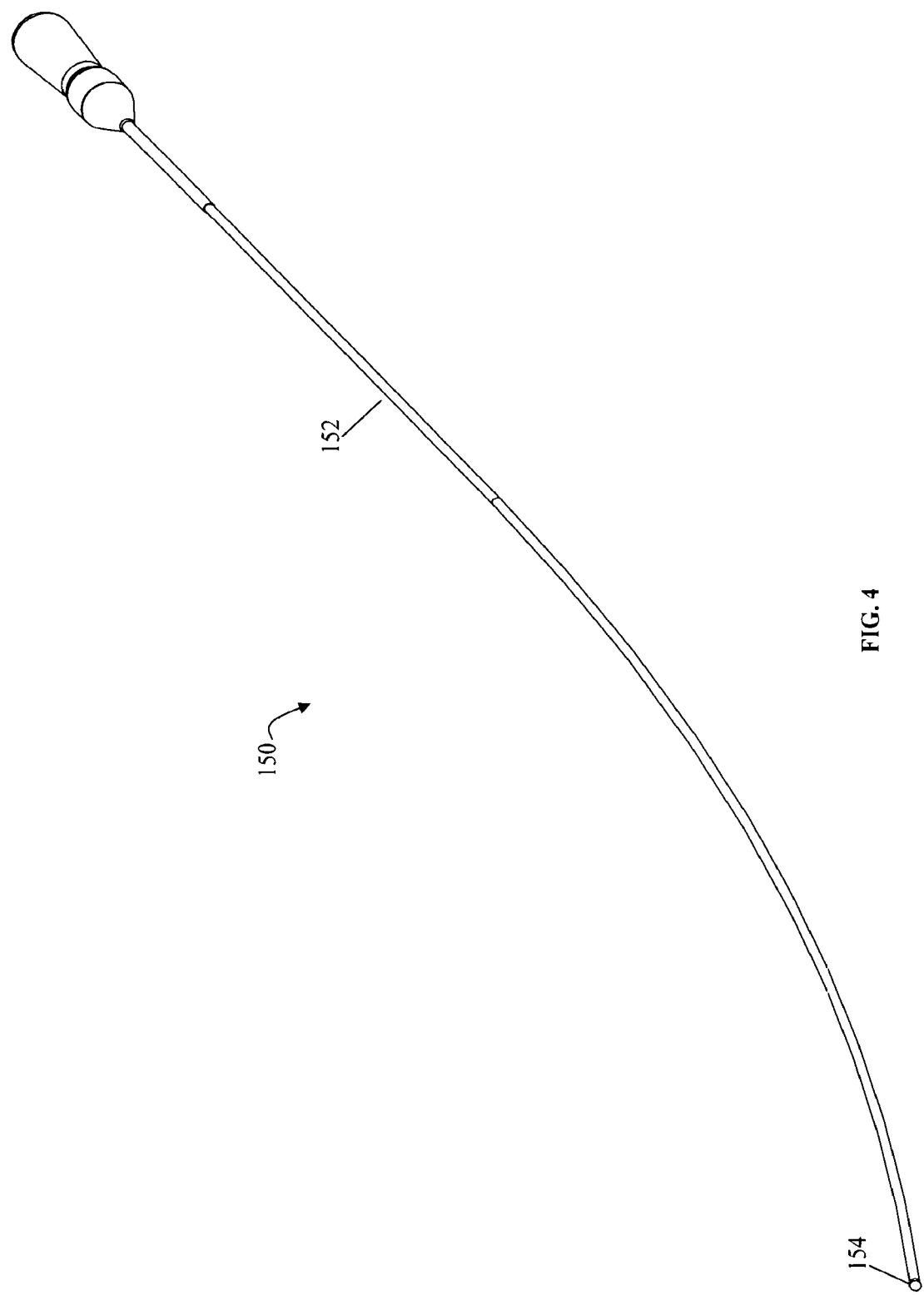
FIG. 4 shows a perspective view of a light source for use with a device for repairing a weakened or fractured bone of the presently disclosed embodiments.

FIG. 4 in conjunction with FIG. 1 shows a light source 150 for use with the device 100 of the presently disclosed embodiments. The light source 150 is used to harden the reinforcing material that has been infused into the balloon portion 103 of the delivery catheter 110. The light source 150 includes a light pipe 152 which terminates in an optical lens 154. Energy emitted from the light pipe 152 is projected through the optical lens 154 and guided into the balloon portion 103 of the delivery catheter 110. The optical lens 154 may be convex, concave or planar. The optical lens 154 is curved to converge or diverge the transmitted energy from the light pipe 152. In an embodiment, the optical lens 154 is made out of a plastic material such as Acrylic (PMMA), Polycarbonate (PC), Polystyrene (PS), or other similar materials known to those in the art such as Cyclic Olefin Copolymer (COC), and Amorphous Polyolefin (Zeonex). In an embodiment, the optical lens 154 is made out of a glass material such as quartz.

The light source 150 is introduced into a side arm of the adapter 115 that engages the proximal end 102 of the delivery catheter 110. The light source 150 runs through the elongated shaft 101 of the delivery catheter 110 through the light pipe conduit and up into the proximal end 123 of the balloon portion 103, as shown in FIG. 1. The activation of the light source 150 cures the reinforcing material resulting in the affixing of the balloon portion 103 in an expanded shape. A cure may refer to any chemical, physical, and/or mechanical transformation that allows a composition to progress from a form (e.g., flowable form) that allows it to be delivered through the void in the delivery catheter 110, into a more permanent (e.g., cured) form for final use in vivo. For example, "curable" may refer to uncured composition, having the potential to be cured in vivo (as by catalysis or the application of a suitable energy source), as well as to a composition in the process of curing (e.g., a composition formed at the time of delivery by the concurrent mixing of a plurality of composition components).

In an embodiment, the reinforcing material is a light cure adhesive or ultraviolet (UV) adhesive. Examples of light cured materials include those commercially available from Loctite of Henkel Corporation, located in Rocky Hill, Conn. and those commercially available from DYMAX Corporation, located in Torrington, Conn. A benefit of UV curing is that it is a cure-on-demand process and that adhesives may be free of solvents and include environmentally friendly resins that cure in seconds upon exposure to long wave UV light or visible light. Different UV adhesives use photoinitiators sensitive to different ranges of UV and visible light. Being very energetic, UV light can break chemical bonds, making molecules unusually reactive or ionizing them, in general changing their mutual behavior. Visible light, for example, visible blue light, allows materials to be cured between substrates that block UV light but transmits visible light (e.g., plastics). Visible light penetrates through the adhesive to a greater depth. Since the visible light penetrates through the adhesive, curing of the adhesive increases as a greater portion of the electromagnetic spectrum is available as useful energy. Additives may be used with the UV adhesive delivery system, including, but not limited to drugs (for example, antibiotics), proteins (for example, growth factors) or other natural or synthetic additives.

The electromagnetic spectrum is the range of all possible electromagnetic radiation. The electromagnetic spectrum of an object is the frequency range of electromagnetic radiation that the object emits, reflects, or transmits. The electromagnetic spectrum extends from just below the frequencies used for modern radio (at the long-wavelength end) to gamma radiation (at the short-wavelength end), covering wavelengths from thousands of kilometers down to fractions of the size of an atom. In an embodiment, the UV adhesive is a single-component, solvent-free adhesive that will not cure until a UV light engages the adhesive, and when that occurs, the adhesive will cure in seconds to form a complete bond with a shear strength. In an embodiment, the reinforcing material exhibits a shrinkage upon cure of about 2 to about 3 percent.

UV light wavelength ranges from about 1 nm to about 380 nm, and can be subdivided into the following categories: near UV (380-200 nm wavelength; abbreviated NUV), far or vacuum UV (200-10 nm; abbreviated FUV or VUV), and extreme UV (1-31 nm; abbreviated EUV or XUV). Similarly, visible light has a wavelength spectrum of between about 380 to about 780 nm. Those skilled in the art will recognize that some UV adhesives may be activated by UV light, visible light, x-rays, gamma rays, microwaves, radio waves, long waves or any light having a wavelength less than about 1 nm, between about 1 nm and about 380 nm, between about 380 nm and about 780 nm, or greater than 780 nm, as not all embodiments are intended to be limited in that respect.

Using a UV light, the reinforcing material ensures there is no or minimal thermal egress and that the thermal egress may not be long in duration. More specifically, there is no chemical composition or mixing of materials. Using the UV light to cure the reinforcing material assists in holding broken bones in place, filling of the balloon portion, and viewing under a C arm imaging system. The reinforcing materials cure in such a way that is sufficient to hold a bone in the correct orientation. More specifically, the ability to inflate, set, adjust, orient bones, and the resulting union of the bone are available prior to hardening the reinforcing material. The introduction of the UV light starts the photoinitiator and the UV adhesive hardens. Once the UV light is introduced, the adhesive inside the balloon portion hardens and the adhesives inside are affixed in place. Until the UV light is introduced, the bone placement is not disturbed or rushed as there is no hardening of the adhesives until the light is introduced, the balloon portion may be inflated or deflated due to the viscosity of the adhesive. The adhesive may be infused or removed from the balloon portion due to the low viscosity of the adhesive. In an embodiment, the viscosity of the reinforcing material has a viscosity of about 1000 cP or less. In an embodiment, the reinforcing material has a viscosity ranging from about 650 cP to about 450 cP. Not all embodiments are intended to be limited in this respect and some embodiments may include reinforcing materials having a viscosity exactly equal to or greater than 1000 cP. In an embodiment, a contrast material may be added to the reinforcing material without significantly increasing the viscosity. Contrast materials include, but are not limited to, barium sulfate, tantalum, or other contrast materials known in the art.

Several epoxies known in the art are suitable for use as bone reinforcing materials and vary in viscosity, cure times, and hardness (durometer or shore) when fully cured. A durometer of a material indicates the hardness of the material, defined as the material's resistance to permanent indentation. Depending on the amount of resultant support that is necessary for a given bone fracture, a specific durometer UV adhesive may be chosen. Alternately, multiple UV adhesives having varying durometers may be chosen for the repair of a bone fracture and be within the scope and spirit of the presently disclosed embodiments. The durometer of a material may be altered to achieve either greater rigidity or a more malleable result. The mechanical properties of the epoxies may dictate using methods/measures that are typical for high-strength and high-impact materials including but not limited to, tensile strength and tensile modulus, tensile strength tests, ultimate modulus, Poisson's ratio, hardness measurements like Vickers and Charpy Impact which measures yield strength and toughness.

In an embodiment, the reinforcing material is cured by chemical activation or thermal activation. Chemical activation includes but is not limited to water or other liquids. In an embodiment, the reinforcing material is a drying adhesive which has a polymer dissolved in a solvent such that as the solvent evaporates, the adhesive hardens. In an embodiment, the reinforcing material is a hot or thermoplastic adhesive such that as the adhesive cools, the adhesive hardens.

The reinforcing material is not limited to the embodiments described herein and may be any material that reinforces the bone. Some materials may require or be enhanced by curing via any means, such as UV or visible light, heat, and/or addition or removal of a chemical or substance, may utilize any outside or internal processes to cure the material, or may not require curing.

In an embodiment, carbon nanotubes (CNTs) are added to the reinforcing material to increase the strength of the material. Carbon nanotubes are an allotrope of carbon that take the form of cylindrical carbon molecules and have novel strength properties. Carbon nanotubes exhibit extraordinary strength. Nanotubes are members of the fullerene structural family, which also includes buckyballs. Whereas buckyballs are spherical in shape, a nanotube is cylindrical with at least one end typically capped with a hemisphere of the buckyball structure. Nanotubes are composed entirely of sp2 bonds, similar to those of graphite. This bonding structure, which is stronger than the sp3 bonds found in diamond, provides the molecules with their unique strength. Nanotubes naturally align themselves into "ropes" held together by Van der Waals forces. Single walled nanotubes or multi-walled nanotubes may be used to strengthen the reinforcing materials.

Figure 5A:
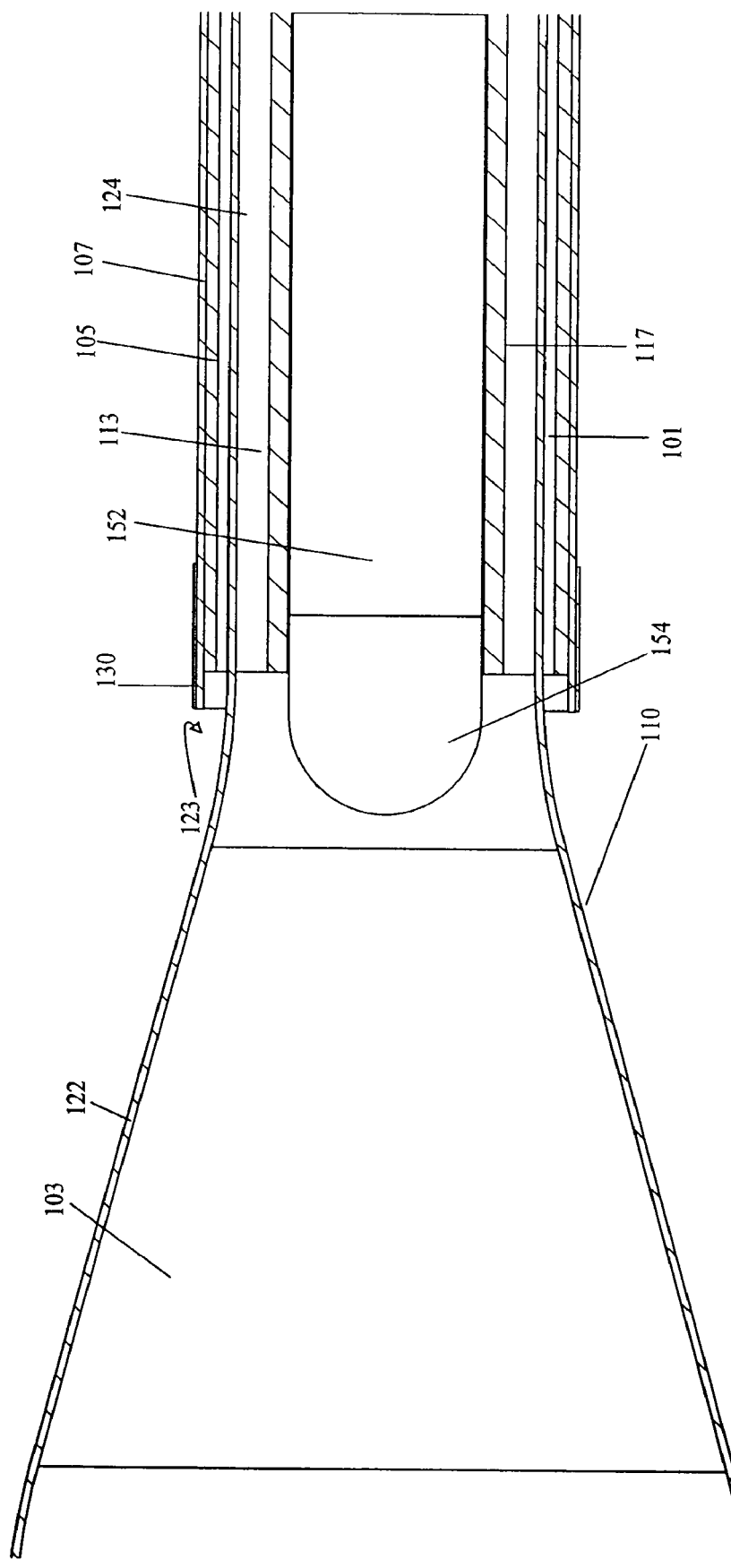
FIG. 5A and FIG. 5B show cross-sectional views of a device for repairing a weakened or fractured bone of the presently disclosed embodiments.
Figure 5B:
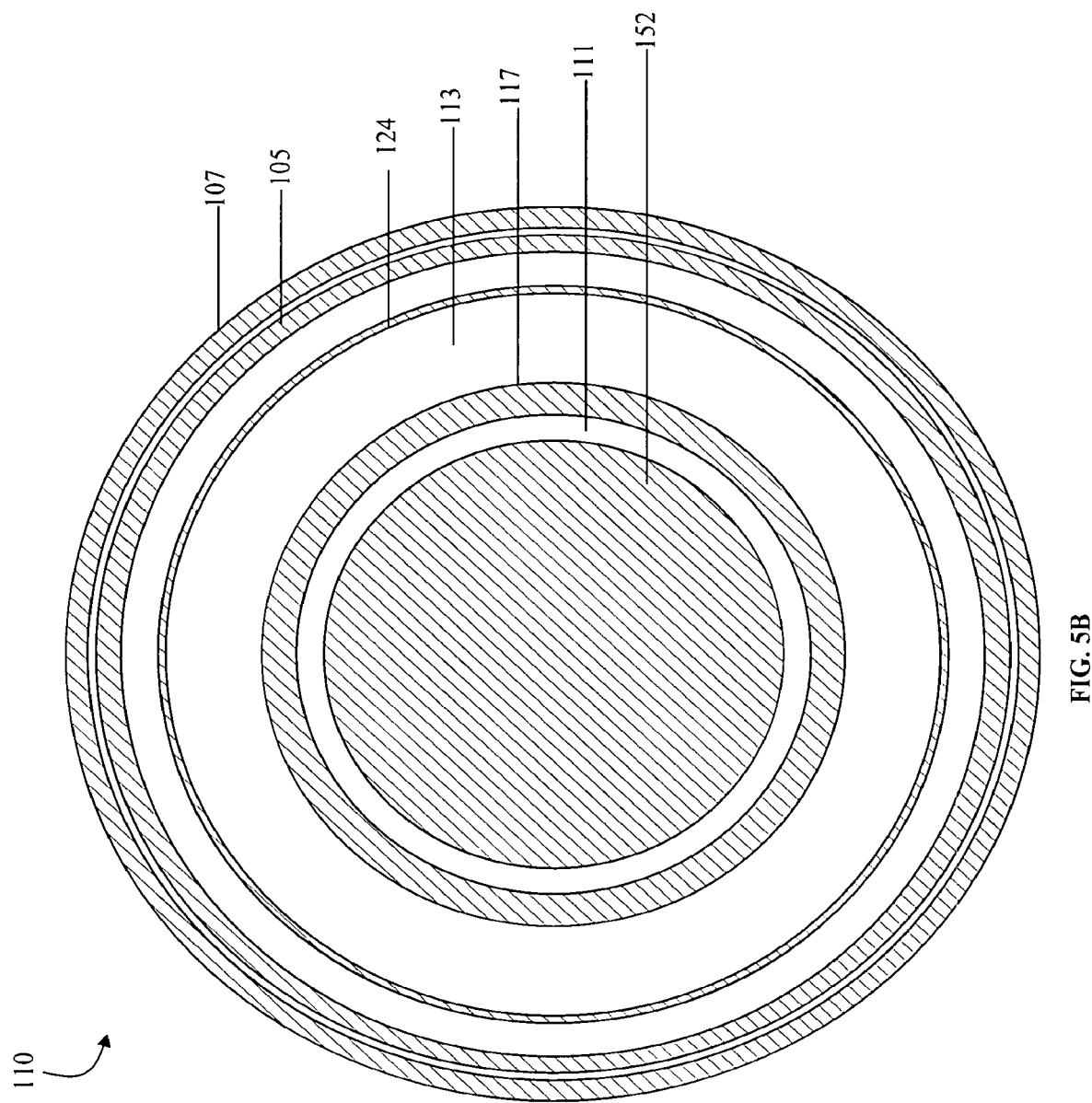

FIG. 5A and FIG. 5B show cross-sectional views of the device 100 showing the light source passing through the light pipe conduit 111 of the delivery catheter 110. The light source includes the light pipe 152 terminating in the optical lens 154. The light source is used to harden the reinforcing material that has been infused into the balloon portion 103 of the delivery catheter 110. Energy emitted from the light pipe 152 is projected through the optical lens 154 and guided into the balloon portion 103 of the delivery catheter 110. The optical lens 154 may be convex, concave or planar. The optical lens 154 is curved to converge or diverge the transmitted energy from the light pipe 152.

In an embodiment, a fracture repair process reinforces a weakened or fractured bone without exposing the bone through a traditional surgical incision. The presently disclosed embodiments use a minimally invasive approach by making a minor incision to gain access to the bone. Minimally invasive refers to surgical means, such as microsurgical, endoscopic or arthroscopic surgical means, that can be accomplished with minimal disruption of the pertinent musculature, for instance, without the need for open access to the tissue injury site or through minimal incisions. Minimally invasive procedures are often accomplished by the use of visualization such as fiber optic or microscopic visualization, and provide a post-operative recovery time that is substantially less than the recovery time that accompanies the corresponding open surgical approach. Benefits of minimally invasive procedures include causing less trauma because there is minimal blood loss, a reduction in surgery and anesthetized time, shortened hospitalization, and an easier and more rapid recovery. In an embodiment, a bone fixator may be placed within an intramedullary cavity of a weakened or fractured bone. By restoring and preserving bone structure, some of the presently disclosed embodiments permit additional future treatment options.

Figure 6A:
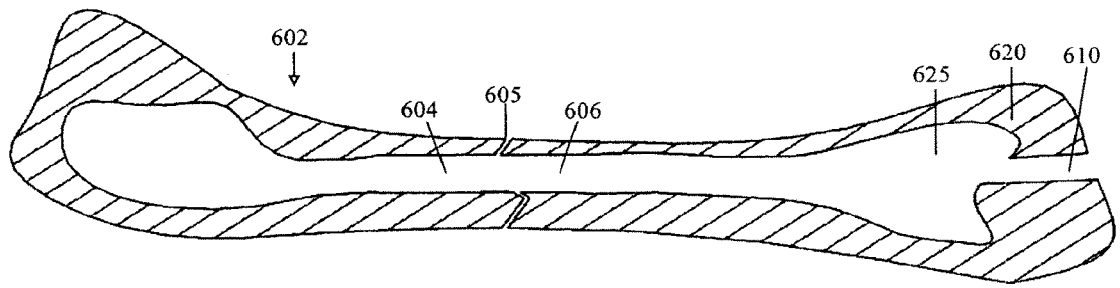
FIG. 6A, FIG. 6B, FIG. 6C, FIG. 6D and FIG. 6E shows the method steps for utilizing a device of the presently disclosed embodiments for repair of a fractured bone.

FIGS. 6A-6E in conjunction with FIG. 1, illustrate the method steps for repairing a fractured bone in a patient's body. A minimally invasive incision (not shown) is made through the skin of the patient's body to expose a fractured bone 602. The incision may be made at the proximal end or the distal end of the fractured bone 602 to expose the bone surface. Once the bone 602 is exposed, it may be necessary to retract some muscles and tissues that may be in view of the bone 602. As shown in FIG. 6A, an access hole 610 is formed in the bone by drilling or other methods known in the art. In an embodiment, the access hole 610 has a diameter of about 3 mm to about 10 mm. In an embodiment, the access hole 610 has a diameter of about 3 mm.

The access hole 610 extends through a hard compact outer layer 620 of the bone into the relatively porous inner or cancellous tissue 625. For bones with marrow, the medullary material should be cleared from the medullary cavity prior to insertion of the device 100. Marrow is found mainly in the flat bones such as hip bone, breast bone, skull, ribs, vertebrae and shoulder blades, and in the cancellous material at the proximal ends of the long bones like the femur and humerus. Once the medullary cavity is reached, the medullary material including air, blood, fluids, fat, marrow, tissue and bone debris should be removed to form a void. The void is defined as a hollowed out space, wherein a first position defines the most distal edge of the void with relation to the penetration point on the bone, and a second position defines the most proximal edge of the void with relation to the penetration site on the bone. The bone may be hollowed out sufficiently to have the medullary material of the medullary cavity up to the cortical bone removed. There are many methods for removing the medullary material that are known in the art and within the spirit and scope on the presently disclosed embodiments. Methods include those described in U.S. Pat. No. 4,294,251 entitled "Method of Suction Lavage," U.S. Pat. No. 5,554,111 entitled "Bone Cleaning and Drying system," U.S. Pat. No. 5,707,374 entitled "Apparatus for Preparing the Medullary Cavity," U.S. Pat. No. 6,478,751 entitled "Bone Marrow Aspiration Needle," and U.S. Pat. No. 6,358,252 entitled "Apparatus for Extracting Bone Marrow."

Figure 6B:
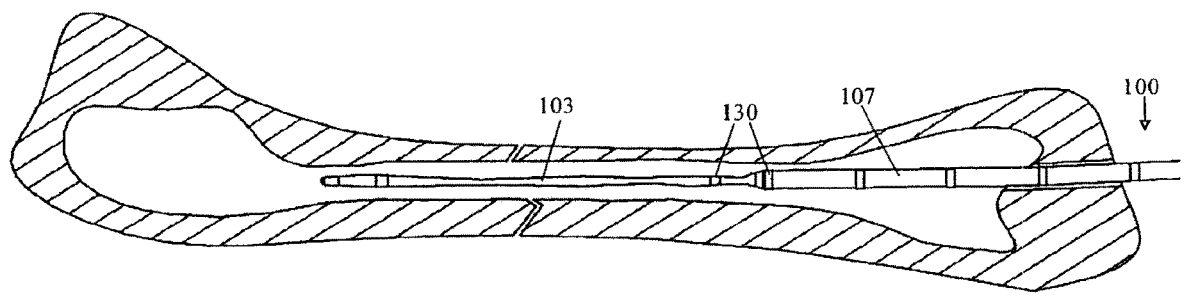
Figure 6C:
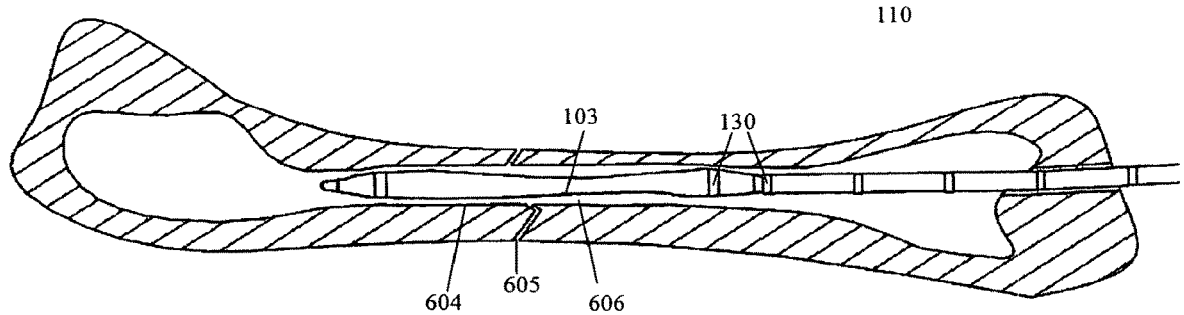

A guidewire (not shown) may be introduced into the bone 602 via the access hole 610 and placed between bone fragments 604 and 606 of the bone 602 to cross the location of a fracture 605. The guidewire may be delivered into the lumen of the bone 602 and crosses the location of the break 605 so that the guidewire spans multiple sections of bone fragments. As shown in FIG. 6B, the balloon portion 103 of the device 100 for repairing a fractured bone, which is constructed and arranged to accommodate the guidewire, is delivered over the guidewire to the site of the fracture 605 and spans the bone fragments 604 and 606 of the bone 602. Once the balloon portion 103 is in place, the guidewire may be removed. The location of the balloon portion 103 may be determined using at least one radiopaque marker 130 which is detectable from the outside or the inside of the bone 602. For example, as shown in the embodiment depicted in FIG. 6, radiopaque markers 130, which are visible from outside of the body using x-ray or other detection means, are located along both the balloon portion 103 and the slip sleeve 107 of the delivery catheter 110 to help align and position the device 100. Once the balloon portion 103 is in the correct position within the fractured bone 602, the device 100 is attached to a delivery system which contains a reinforcing material. The reinforcing material is then infused through a void in the delivery catheter 110 and enters the balloon portion 103 of the device 100. This addition of the reinforcing material within the balloon portion 103 causes the balloon portion 103 to expand, as shown in FIG. 6C. As the balloon portion 103 is expanded, the fracture 605 is reduced. In an embodiment, the reinforcing material is a UV curable glue which requires a UV light source to cure the adhesive. In an embodiment, a central space may remain in the balloon portion 103 which may be filled in order to provide extra strength and support to the fractured bone 602. An optical rod or similar device may be positioned in the central space and turned on or illuminated. An optical rod or similar device can be made of fiber, silica, quartz, sapphire or similar materials. The UV light will then harden the UV curable glue in the balloon portion 103. The end of the optical rod may be cut and remain in the balloon portion 103 to provide increased rigidity.

Figure 6D:
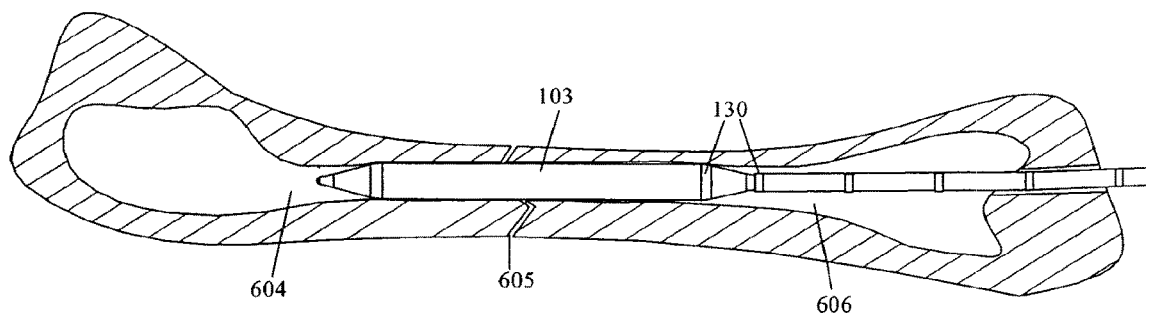
Figure 6E:
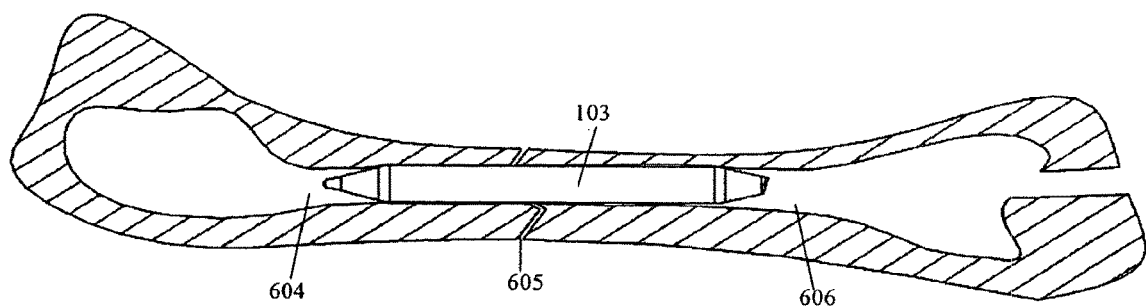

Once orientation of the bone fragments 604 and 606 are confirmed to be in a desired position, the UV curable glue may be hardened within the balloon portion 103, as shown in FIG. 6D, such as by illumination with a UV emitting light source. After the UV curable glue has been hardened, the light source may be removed from the device 100. The balloon portion 103 once hardened, may be released from the delivery catheter 110 by known methods in the art. In an embodiment, the delivery catheter 110 is cut to separate the balloon portion 103 from the elongated shaft 101. A device slides over the delivery catheter 110 and allows a right angle scissor to descend through the delivery catheter 110 and make a cut. The location of the cut may be determined by using a fluoroscope or an x-ray. In an embodiment, the cut location is at the junction where the elongated shaft 101 meets the balloon portion 103.

In an embodiment, the device 100 is used to treat a hand or wrist fracture. The wrist is a collection of many joints and bones that allow use of the hands. The wrist has to be mobile while providing the strength for gripping. The wrist is complicated because every small bone forms a joint with its neighbor. The wrist comprises at least eight separate small bones called the carpal bones, that connect the two bones of the forearm, called the radius and the ulna, to the bones of the hand and fingers. The wrist may be injured in numerous ways. Some injuries seem to be no more than a simple sprain of the wrist when the injury occurs, but problems can develop years later. A hand fracture may occur when one of the small bones of the hand breaks. The hand consists of about 38 bones and any one of these bones may suffer a break. The palm or midhand is made up of the metacarpal bones. The metacarpal bones have muscular attachments and bridge the wrist to the individual fingers. These bones frequently are injured with direct trauma such as a crush from an object or most commonly the sudden stop of the hand by a wall. The joints are covered with articular cartilage that cushions the joints. Those skilled in the art will recognize that the disclosed device and methods can be used for to treat fractures to other bones, such as radius, ulna, clavicle, metacarpals, phalanx, metatarsals, phalanges, tibia, fibula, humerus, spine, ribs, vertebrae, and other bones and still be within the scope and spirit of the disclosed embodiments.

The presently disclosed embodiments may be used to treat a clavicle fracture, resulting in a clavicle reduction. The clavicle or collar bone is classified as a long bone that makes up part of the shoulder girdle (pectoral girdle). Present methods to affix a broken clavicle are limited. The clavicle is located just below the surface of the skin, so the potential for external fixation including plates and screws is limited. In addition, the lung and the subclavian artery reside below the collar bone so using screws is not an attractive option. Traditional treatment of clavicle fractures is to align the broken bone by putting it in place, provide a sling for the arm and shoulder and pain relief, and to allow the bone to heal itself, monitoring progress with X-rays every week or few weeks. There is no fixation, and the bone segments rejoin as callous formation and bone growth bring the fractured bone segments together. During healing there is much motion at the fracture union because there is not solid union and the callous formation often forms a discontinuity at the fracture site. A discontinuity in the collar bone shape often results from a clavicle fracture.

The presently disclosed embodiments and methods treat a clavicle fracture in a minimally invasive manner and may be used for a clavicle reduction or collar bone reduction. A benefit of using the disclosed device to repair a collar bone is the repair minimizes post repair misalignment of collar bone. A benefit of using the disclosed device to repair a clavicle is to resolve the patient's pain during the healing process.

FIGS. 7A, 7B and 7C, in conjunction with FIGS. 8A, 8B and 8C, show a device 100 of the presently disclosed embodiments for use in repairing a fractured metacarpal bone 702 in a finger 710 in a hand 700 of a patient. As shown, the fractured metacarpal bone 702 has been split into two fragments, 704 and 706, at a break site 705. As shown in FIG. 8A, the balloon portion of the device 100 is delivered to the site of the fracture 75 and spans the bone fragments 74 and 706 of the bone 702. The location of the balloon portion may be determined using at least one radiopaque marker which is detectable from the outside or the inside of the bone 702. Once the balloon portion is in the correct position within the fractured bone 702, the device 100 is attached to a delivery system which contains a reinforcing material. The reinforcing material is then infused through a void in the delivery catheter and enters the balloon portion of the device 100. This addition of the reinforcing material within the balloon portion causes the balloon portion to expand, as shown in FIG. 8B. As the balloon portion is expanded, the fracture 705 is reduced. In an embodiment, the reinforcing material is a UV curable glue which requires a UV light source to cure the adhesive. The UV light will then harden the UV curable glue in the balloon portion.

Once orientation of the bone fragments 704 and 706 are confirmed to be in a desired position, the UV curable glue may be hardened within the balloon portion, such as by illumination with a UV emitting light source. After the UV curable glue has been hardened, the light source may be removed from the device 100. The balloon portion once hardened, may be released from the delivery catheter by known methods in the art, as shown in FIG. 8C. In an embodiment, the delivery catheter is cut to separate the balloon portion from the elongated shaft.

All patents, patent applications, and published references cited herein are hereby incorporated by reference in their entirety. It will be appreciated that several of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

What is claimed is:

1. A device for repairing a bone comprising
a balloon portion releasably engaging a distal end of a delivery catheter; and
an inner lumen of the delivery catheter engaging the balloon portion such that a light energy can be delivered to the balloon portion to cure at least one reinforcing material curable by the light energy;
wherein the balloon portion is configured to move from a deflated state to an inflated state when the at least one reinforcing material is added into the balloon portion such that the inflated state of the balloon portion can be adjusted to orient the bone to a desired position by altering an amount of the at least one reinforcing material in the balloon portion by adding or withdrawing the at least one reinforcing material into and out of the balloon portion due to the viscosity of the reinforcing material, the viscosity of the reinforcing material being 1000 cP or less,
wherein the balloon portion is configured for placement into a cavity of the bone.

2. The device of claim 1, wherein the bone is selected from a group consisting of one of a metacarpal bone, femur, tibia, fibula, humerus, ulna, radius, metatarsals, phalanx, phalanges, ribs, spine, vertebrae or clavicle.

3. The device of claim 1, wherein the balloon portion is constructed to transit within the cavity of the bone.

4. The device of claim 1, wherein the balloon portion does not extend through one or more hole, one or more crack or both, in the bone.

5. The device of claim 1, wherein the balloon portion includes one or more valves.

6. The device of claim 1, wherein a radiopaque bead is positioned at a distal end of the balloon portion for alignment of the device during fluoroscopy.

7. The device of claim 1, wherein a separation area is located at a junction between a distal end of a portion of the balloon portion and the elongated shaft and the separation area includes a length up to about 1 inch.

8. The device of claim 7, wherein the separation area includes an illumination band extending around the delivery catheter and having a stress concentrator.

9. The device of claim 1, wherein the inner lumen of the delivery catheter is configured to engage the balloon portion to minimize thermal egress of the light energy to surrounding tissue from the balloon portion.

10. The device of claim 1, further comprising an optical rod configured to extend through the inner lumen of the delivery catheter to guide the light energy into the balloon portion.

11. A kit for repairing a weakened or fractured bone, the kit comprising:
a delivery catheter having an elongated shaft with a proximal end, a distal end, and a longitudinal axis therebetween;
a balloon portion designed to releasably engage the delivery catheter;
at least one reinforcing material curable by light energy configured to pass through an inner void of the delivery catheter and into the balloon portion; and
wherein the balloon portion is configured to move from a deflated state to an inflated state when the at least one reinforcing material is added into the balloon portion such that the inflated state of the balloon portion can be adjusted to orient the bone to a desired position by altering an amount of the at least one reinforcing material in the balloon portion by adding or withdrawing the at least one reinforcing material into and out of the balloon portion due to the viscosity of the reinforcing material, the viscosity of the reinforcing material being 1000 cP or less, the reinforcing material being curable by a light energy delivered through the catheter to the balloon.

12. The kit of claim 11, further comprising a light source for providing the light energy to a light pipe configured to extend through an inner lumen of the delivery catheter into the balloon portion to guide the light energy into the balloon portion to cure the reinforcing material.

13. The kit of claim 12, further comprising an adapter to be releasably engaged to the proximal end of the delivery catheter for receiving the light pipe and the at least one reinforcing material.

14. The kit of claim 11, further comprising a plurality of balloon portions of varying sizes.

15. The kit of claim 11, further comprising a device for cutting the balloon portion from the delivery catheter.

16. The kit of claim 11, wherein the inner lumen of the delivery catheter is configured to engage the balloon portion to minimize thermal egress of the light energy to surrounding tissue from the balloon portion.

17. A method for repairing a weakened or a fractured bone comprising:
positioning a balloon portion releasably engaging a delivery catheter within a cavity of the bone, wherein the delivery catheter has an inner void for passage of a light cure adhesive to the balloon portion and an inner lumen for passage of a light energy to the balloon portion;
expanding the balloon portion by infusion of the light cure adhesive into the inner void of the delivery catheter and into the balloon portion;
adjusting the expanded state of the balloon portion to orient bone to a desired position by altering an amount of the light cure adhesive in the balloon portion by adding or withdrawing the light cure adhesive into and out of the balloon portion due to the viscosity of the light cure adhesive, the viscosity of the light cure adhesive being 1000 cP or less; and
delivering light energy into the balloon portion to cure the light cure adhesive within the balloon portion.

18. The method of claim 17, further comprising determining a position of the balloon portion and an expansion of the balloon portion within the cavity of the bone by monitoring one or more radiopaque markers on the balloon portion.

19. The method of claim 17, wherein the inner lumen engages the balloon portion to minimize thermal egress of light energy to surrounding tissue from the balloon portion.

20. The method of claim 17, further comprising inserting an optical rod through the inner lumen of the delivery catheter and into the balloon portion to guide the light energy therein.

\* \* \* \* \*